US011970501B2

(12) United States Patent
Sun et al.

(10) Patent No.: US 11,970,501 B2
(45) Date of Patent: Apr. 30, 2024

(54) HIGHLY POLARIZABLE 3D ORGANIC PEROVSKITES AND ELECTRO-OPTIC MATERIALS COMPRISING SAME

(71) Applicant: Huawei Technologies Canada Co., Ltd., Kanata (CA)

(72) Inventors: Meng-Jia Sun, Würzburg (DE); Chao Zheng, Hamilton (CA); Sjoerd Hoogland, Toronto (CA); Edward Hartley Sargent, Toronto (CA)

(73) Assignee: HUAWEI TECHNOLOGIES CANADA CO., LTD., Kanata (CA)

( * ) Notice: Subject to any disclaimer, the term of this patent is extended or adjusted under 35 U.S.C. 154(b) by 47 days.

(21) Appl. No.: 17/464,598

(22) Filed: Sep. 1, 2021

(65) Prior Publication Data
US 2022/0098209 A1 Mar. 31, 2022

Related U.S. Application Data

(60) Provisional application No. 63/073,718, filed on Sep. 2, 2020.

(51) Int. Cl.
*C07D 487/08* (2006.01)
*H10K 85/30* (2023.01)
*G02F 1/061* (2006.01)

(52) U.S. Cl.
CPC ........... *C07D 487/08* (2013.01); *H10K 85/30* (2023.02); *G02F 1/061* (2013.01)

(58) Field of Classification Search
CPC ............................. C07D 487/08; H10K 85/50
See application file for complete search history.

(56) References Cited

U.S. PATENT DOCUMENTS 4,216,322 A    8/1980   Temme

FOREIGN PATENT DOCUMENTS

CA    2283018 A1    3/2000
WO    2014068341 A2   5/2014

OTHER PUBLICATIONS

Song et al, Metal-Free Halide Perovskite Single Crystals with Very Long Charge Lifetimes for Efficient X-ray imaging, 2020, Adv. Mater., vol. 32, p. 1-8 (Year: 2020).*
Ehrenreich et al, Mechanical properties of the ferroelectric metal-free perovskite [MDABCO](NH4)I3, 2019, Chem. Commun., vol. 55, p. 3911-3914. (Year: 2019).*
E. L. Wooten, K. M. Kissa, A. Yi-Yan, E. J. Murphy, D. A. Lafaw, P. F. Hallemeier, D. Maack, D. V. Attanasio, D. J. Fritz, G. J. McBrien, D. E. Bossi, IEEE J. Sel. Top. Quantum Electron. 2000, 6, 69.
S. Amiri, S. R. B. Azzuhri, M. A. Jalil, H. M. Hairi, J. Ali, M. Bunruangses, P. Yupapin, Micromachines 2018, 9, 452.
C. Wang, M. Zhang, X. Chen, M. Bertrand, A. S. Ansari, S. Chandrasekhar, P. Winzer, M. M. Lonar, Nature 2018, 562, 101.
A. D. Dupuy, Y. Kodera, J. E. Garay, Adv. Mater. 2016, 28, 7970.
Y. Gao, G. Walters, Y. Qin, B. Chen, Y. Min, A. Seifitokaldani, B. Sun, P. Todorovic, M. I. Saidaminov, A. Lough, S. Tongay, S. Hoogland, E. H. Sargent, Adv. Mater. 2019, 31, 1808336.
R. S. Weis, T. K. Gaylord, Appl. Phys. A 1985, 37, 191.
S. Abel, F. Eltes, J. E. Ortmann, A. Messner, P. Castera, T. Wagner, D. Urbonas, A. Rosa, A. M. Gutierrez, D. Tulli, P. Ma, B. Baeuerle, A. Josten, W. Heni, D. Caimi, L. Czomnomaz, A. A. Demkov, J. Leuthold, P. Sanchis, J. Fompeyrine, Nat. Mater. 2019, 18, 42.
S. Abel, T. Stoferle, C. Marchiori, C. Rossel, M. D. Rossell, R. Erni, D. Caimi, M. Sousa, A. Chelnokov, B. J. Offrein, J. Fompeyrine, Nat. Commun. 2013, 4, 1671.
L. Chen, R. M. Reano, Opt. Express 2012, 20, 4032.
S. R. Marder, L.-T. Cheng, B. G. Tiemann, A. C. Friedli, M. Blanchard-Desce, J. W. Perry, J. Skindhøj, Science 1994, 263, 511.
L. R. Dalton, J. Phys.: Condens. Matter 2003, 15, R897.
S. R. Marder, B. Kippelen, A. K.-Y. Jen, N. Peyghambarian, Nature 1997, 388, 845.
L. R. Dalton, A. W. Harper, B. H. Robinson, Proc. Natl. Acad. Sci. USA 1997, 94, 4842.
C. A. Bremner, M. Simpson, W. T. A. Harrison, J. Am. Chem. Soc. 2002, 124, 10960.
H.-Y. Ye, Y.-Y. Tang, P.-F. Li, W.-Q. Liao, J.-X. Gao, X.-N. Hua, H. Cai, P.-P. Shi, Y.-M. You, R.-G. Xiong, Science 2018, 361, 151.
Y. Gao, S. M. Alsadat, A. Johnston, C. Zheng, G. Walters, Q. Feng, X. Wang, M.-J. Sun, A. M. Najarian, D. Xue, Y.-K. Wang, M. I. Saidaminov, O. Voznyy, S. Hoogland, E. H. Sargent, Electro-optic Modulation using Metal-free Perovskites, ACS Appl. Mater. Interfaces. 2021, 13, 19042.
H. Wang, H. Liu, Z. Zhang, Z. Liu, Z. Lv, T. Li, W. Ju, H. Li, X. Cai, H. Han, npj Comput. Mater. 2019, 5, 17.
F. Wang, Phys. Rev. B 1999, 59, 9733.
H.-Y. Zhang, Y.-Y. Tang, P.-P. Shi, R.-G. Xiong, Acc. Chem. Res. 2019, 52, 1928.
Y. Ai, X.-G. Chen, P.-P. Shi, Y.-Y. Tang, P.-F. Li, W.-Q. Liao, R.-G. Xiong, J. Am. Chem. Soc. 2019, 141, 4474.

(Continued)

*Primary Examiner* — Matthew P Coughlin
*Assistant Examiner* — Karen Cheng

(57) ABSTRACT

The present invention relates to highly polarizable 3D organic perovskites of the general formula $ABX_3$, prepared by introducing halogen functional groups in the A-site cation (in which the A and B sites are occupied by organic cations and the X site is a monovalent non-metallic counterion). The $(DCl)(NH_4)(BF_4)_3$ crystal exhibits a strong linear electrooptic (EO) effect with an effective EO coefficient of 20 pmV$^{-1}$, which is 10 times higher than that of metal halide perovskites. These 3D organic perovskites are solution processed and compatible with silicon, and illustrate the potential of rationally-designed all-organic perovskites for use in on-chip modulators, electro-optic devices, piezoelectric devices, or silicon photonics devices.

5 Claims, 29 Drawing Sheets

(56) References Cited

OTHER PUBLICATIONS

M. W. Lufaso, P. M. Woodward, Acta Crystallogr., Sect. B: Struct. Sci. 2004, 60, 10.
M. Martinez-Lope, M. Casais, M. Fernandez-Diaz, Inorg. Chem. 2000, 39, 917.
C. C. Teng, H. T. Man, Appl. Phys. Lett. 1990, 56(18), 1734.
Y. Shuto, M. Amano, J. Appl. Phys. 1995, 77, 4632.
J. L. Casson, K. T. Gahagan, D. A. Scrymgeour, R. K. Jain, J. M. Robinson, V. Gopalan, R. K. Sander, J. Opt. Soc. Am. B 2004, 21, 1948.
W. Kohn, L. J. Sham, Phys. Rev. 1965, 140, A1133.
J. P. Perdew, K. Burke, M. Ernzerhof, Phys. Rev. Lett. 1996, 77, 3865.
S. Goedecker, M. Teter, J. Hutter, Phys. Rev. B 1996, 54, 1703.
S. Grimme, J. Antony, S. Ehrlich, H. Krieg, J. Chem. Phys. 2010, 132, 154104.
B. G. Lippert, J. H. Parrinello, Michele, Mol. Phys. 1997, 92, 477.
J. VandeVondele, M. Krack, F. Mohamed, M. Parrinello, T. Chassaing, J. Hutter, Comput. Phys. Commun. 2005, 167, 103.
J. Hutter, M. Iannuzzi, F. Schiffmann, J. VandeVondele, WIREs Comput. Mol. Sci. 2014, 4, 15.
S. Luber, J. Chem. Phys. 2014, 141, 234110.
Yang Chen et al., Fluorium-Initiated Dealkylative Cyanation of Thioethers to Thiocyanates, 2019 American Chemical Society, total 7 pages.
Ke Yang et al, Benzisothiazol-3-ones through a Metal-Free Intramolecular N S Bond Formation, 2018 Wiley-VCH Verlag GmbH and Co. KGaA, Weinheim, total 4 pages.
Banks R E et al:"N-Halogeno compounds. Part 20.Vicarious eletrophilicfluorodeuemeuethylation of1 3 5-trimuethoxybenze and2 4 6-trimethoxytoluene with 1-chloromethyl-4-fluoro-1 4-diazoniabicyclo [2.2.2]octane bis (tetrafluoroborate)(Selectfluor/\T/\reagent F-TEDA-BF"4) Journal of Flourineue Chemistry, Elsevier, NL, vol. 96, No. 2, Jul. 4, 1999 (Jul. 4, 1999) pp. 129-133 XP004173701.
Stefan Abeuel et al: "A strongelectro-optically active lead-freefeuerroelectric integrated on silicon" Nature Communications vol. 4, No. 1, Apr. 9, 2013 (Apr. 9, 2013) XP055496297, 6 pages.

\* cited by examiner

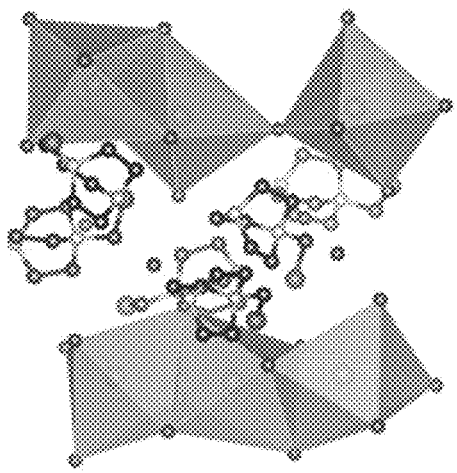
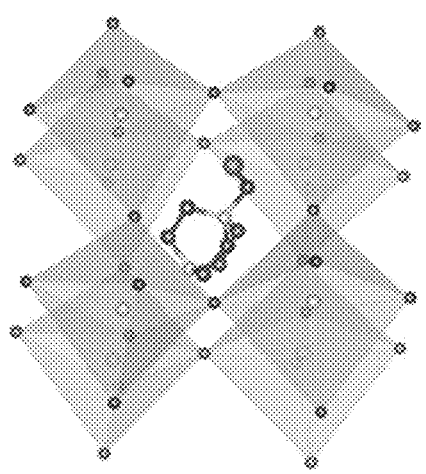
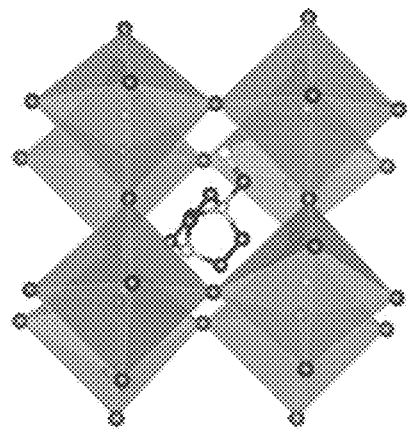
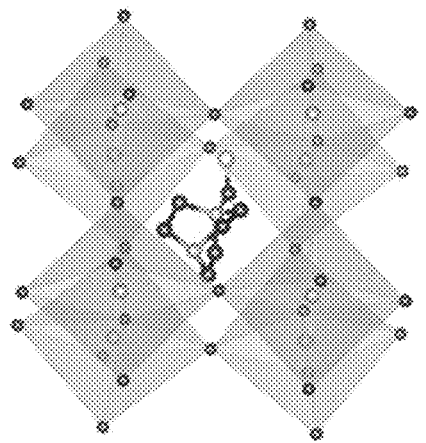
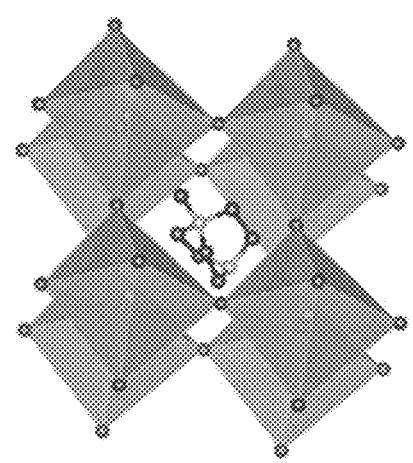
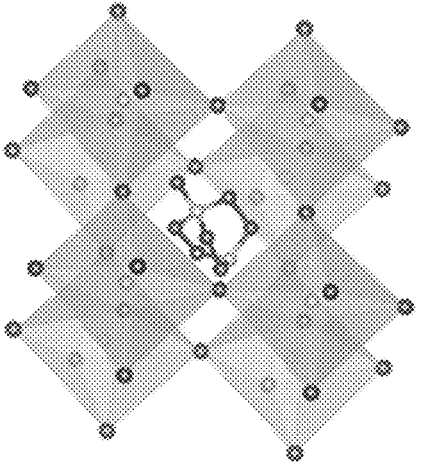
Fig. 1b
Fig. 1c
R = Cl
R = F
R = H

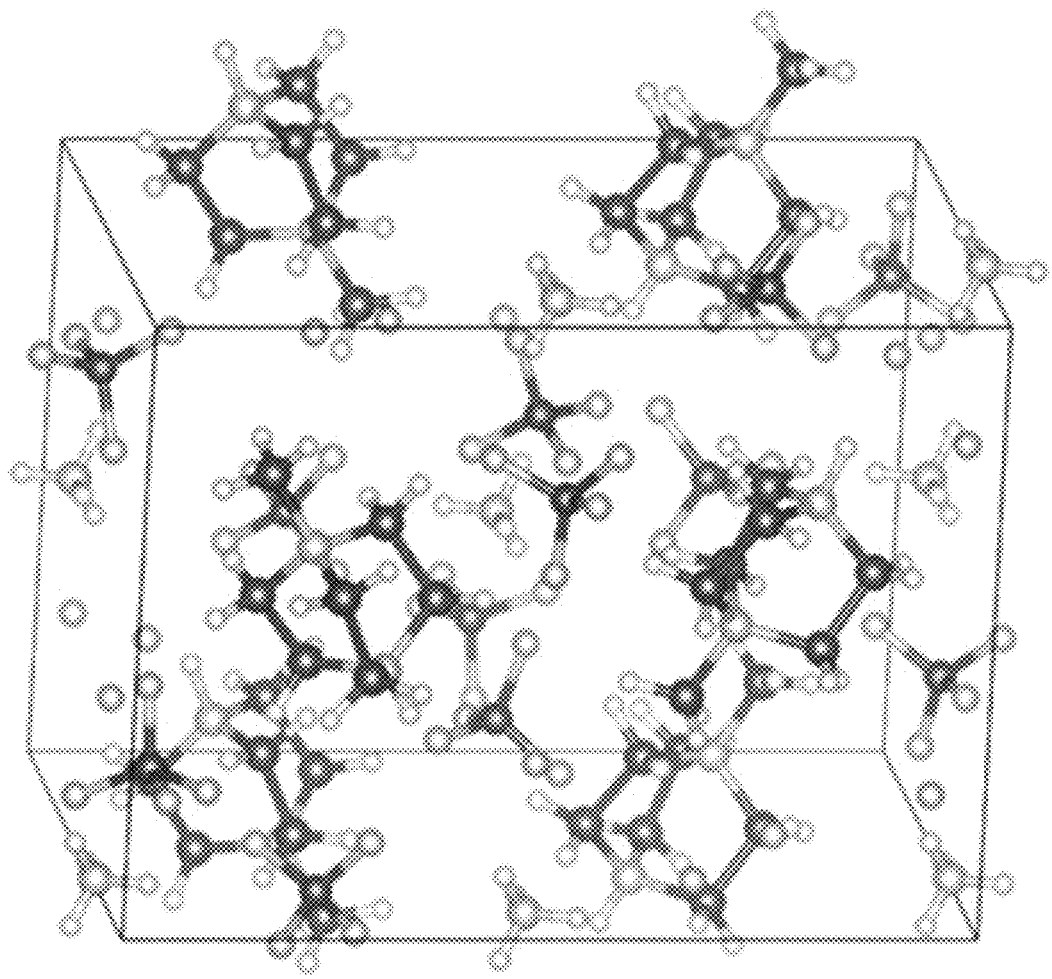
Fig. 2a
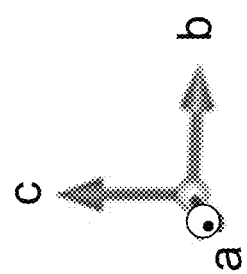

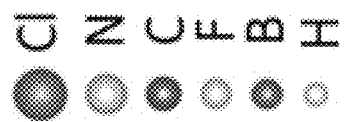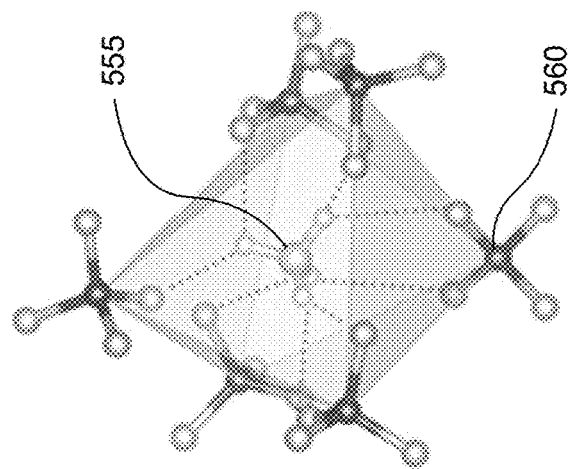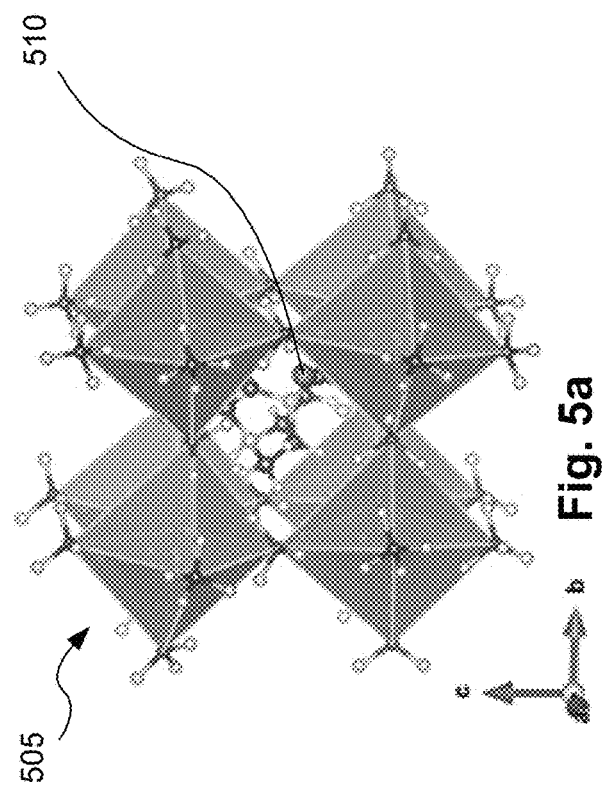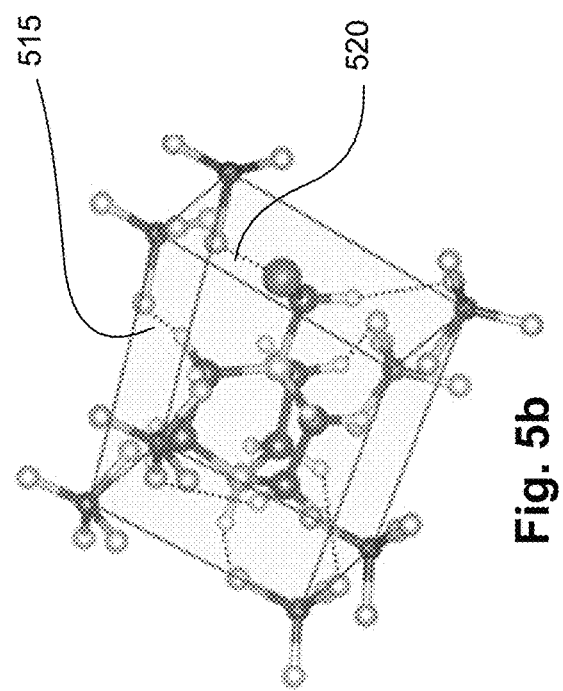
Fig. 5a
Fig. 5b
Fig. 5c

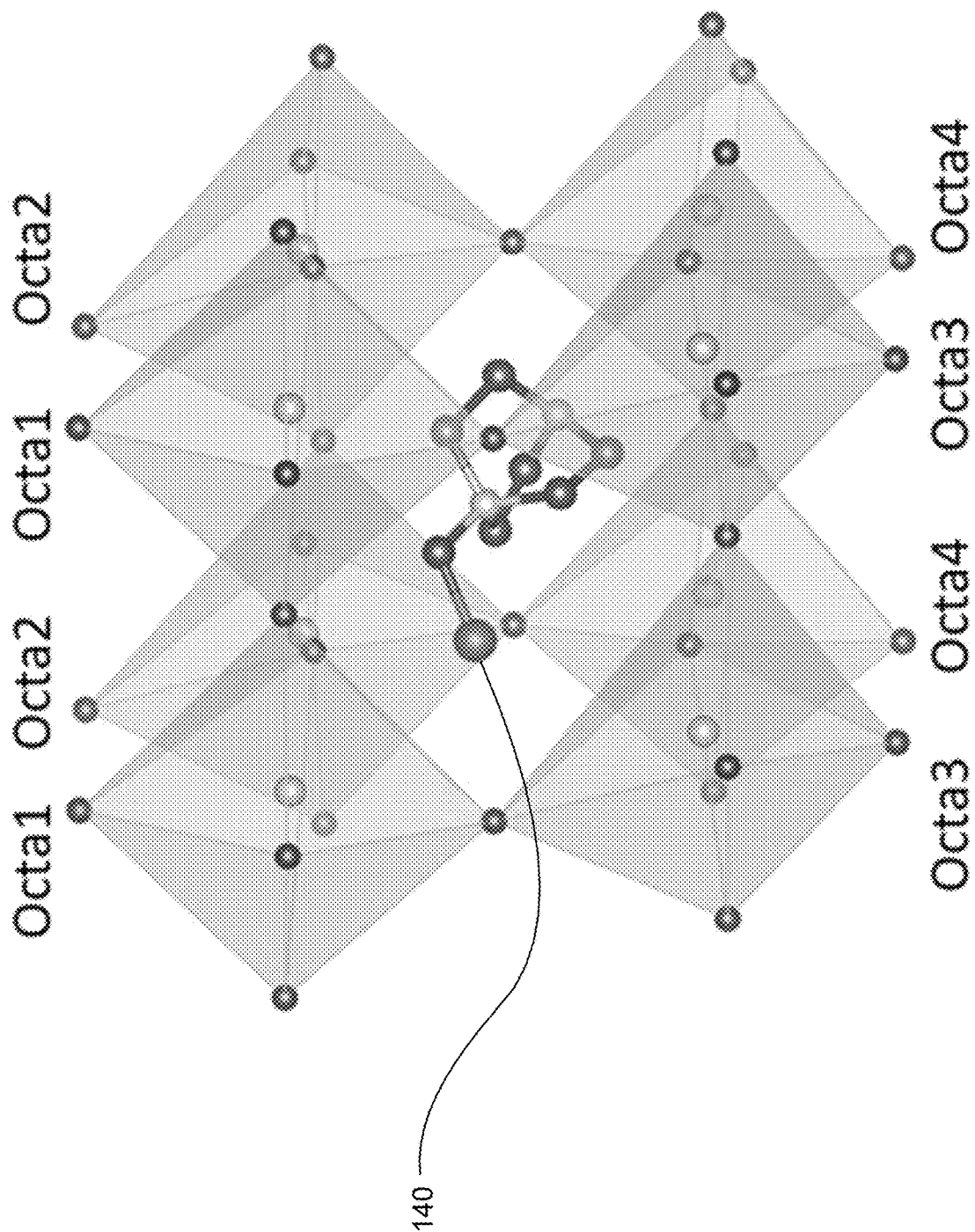

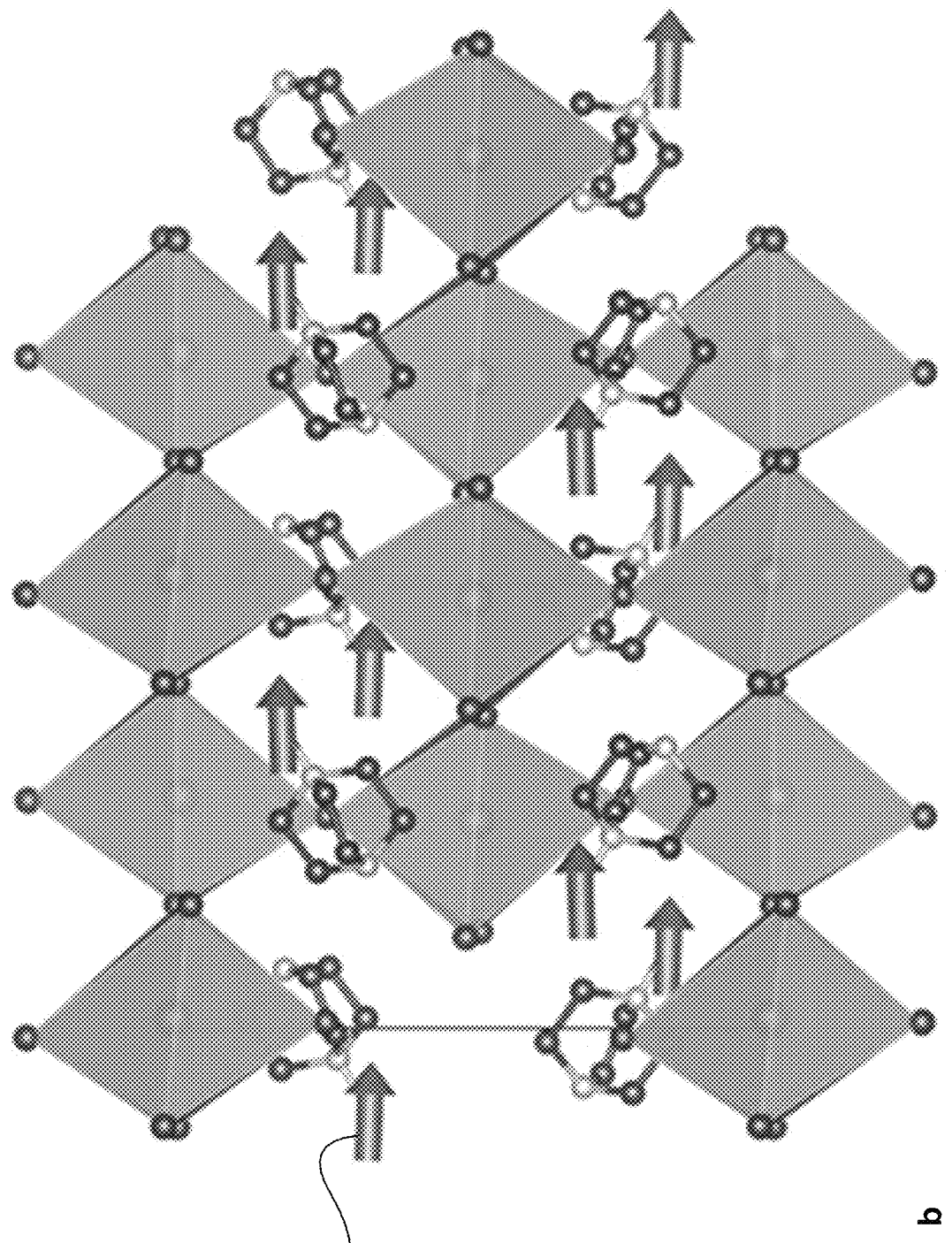
Fig. 8a
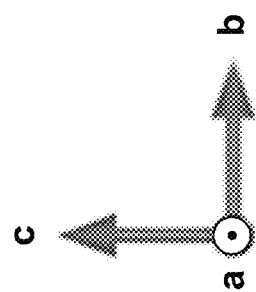

HIGHLY POLARIZABLE 3D ORGANIC PEROVSKITES AND ELECTRO-OPTIC MATERIALS COMPRISING SAME

CROSS-REFERENCE TO RELATED APPLICATIONS

The present application claims the benefit of priority to U.S. Provisional Patent Application Ser. No. 63/073,718, entitled "Linear Electro-Optic Modulation in Highly Polarizable Organic Perovskites," filed Sep. 2, 2020, the contents of which are herein wholly incorporated by reference.

TECHNICAL FIELD OF THE INVENTION

This invention pertains generally to the field of optoelectronic devices and in particular, to electro-optic crystalline materials.

BACKGROUND

In silicon photonics, the conversion of information from the electrical to the optical domain is realized using on-chip light modulators (Ref 1). Electrical-to-optical signal conversion is widely employed in information technology and is implemented using on-chip optical modulators. These devices rely on silicon pn-junctions which modulate the phase of the light under an applied field. Impressive multi-GHz information processing speeds are realized; but the devices require large footprints in light of the weak interaction of light with silicon free carriers.

The linear electro-optic (EO) effect, also known as Pockels effect, relies on noncentrosymmetric crystals whose spontaneous polarization is modulated using an electric field to cause a change in refractive index (Ref 2). Inorganic EO-active crystals are typically based on perovskite oxides, such as lithium niobite and barium titanate (Ref 3), but their integration is a challenge with silicon photonics chips (Ref. 4). Inorganic nonlinear crystals such as $LiNbO_3$ are integrated with silicon photonic chips only using complex and costly approaches, and hybrid silicon-$LiNbO_3$ optical modulators show either low bandwidth or high operating voltage.

Organic nonlinear chromophores exhibit tunable polarized pi-scaffolds, which result in large changes in refractive index at high modulation speeds (Ref. 5), and are solution-processed and compatible with silicon; however, they often suffer a loss of polarization in the solid state due to the formation of centrosymmetric crystal packing caused by dipole-dipole interactions (Ref. 6). Although the noncentrosymmetric orientation of organic chromophores can be realized by poling at elevated temperature, in many cases, the macroscopic nonlinear susceptibilities fell short of expectations due to the disorientation of molecules in low temperature (Ref 5c).

There therefore remains a need for electro-optic active materials that have the convenience of being solution processed and that are also stable over the long-term without losing polarization.

This background information is provided to reveal information believed by the applicant to be of possible relevance to the present invention. No admission is necessarily intended, nor should be construed, that any of the preceding information constitutes prior art against the present invention.

SUMMARY

An object of the present invention is to provide a highly polarizable 3D organic perovskite electro-optic material. In accordance with an aspect of the present invention, there is provided a 3D organic perovskite having the Formula (I) $ABX_3$, wherein A has the formula $DR^{2+}$, wherein $DR^{2+}$ is:

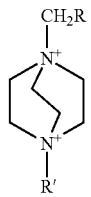

wherein R is F, Cl, Br, CN, or OH; and R' is H or $CH_3$; B is $NH_4^+$; and X is $BF_4^-$ or $PF_6^-$.

In accordance with another aspect of the present invention, there is provided use of a 3D organic perovskite in accordance with the present invention in a silicon photonic device, in an electro-optic device or in a piezoelectric device.

In accordance with another aspect of the present invention, there is provided a process for preparing 3D (DR)$(NH_4)(BF_4)_3$ perovskite crystals, the process comprising the steps of: providing an aqueous solution of stoichiometric amounts of DR, wherein R is F or Cl, and $NH_4BF_4$ in excess $HBF_4$; heating the solution to 80□ for 1 h; and cooling the solution to room temperature at a rate of 4 K/h to yield centimeter-sized transparent crystals.

BRIEF DESCRIPTION OF THE DRAWINGS

FIG. 1B illustrates a series of perovskite structured crystals in which the X sites are occupied by I$^-$ ions and R in the A-site cation is H (left), F (middle) and Cl (right).

FIG. 1C illustrates a series of perovskite structured crystals in which the X sites are occupied by $BF_4^-$ and R in the A-site cation is H (left), F (middle) and Cl (right), in accordance with embodiments of the invention.

FIGS. 2A-C illustrate a unit cell, 3D crystal packing, and an x-ray diffraction (XRD) spectrum of (DH)$(NH_4)(BF_4)_3$.

FIGS. 5A-C illustrate crystal properties of (DCl)$(NH_4)(BF_4)_3$, in accordance with one embodiment of the invention, including (a) 3D single crystal packing, (b) Hydrogen and halogen bonding in the cavity between $DCl^{2+}$ and $BF_4^-$, and (c) hydrogen bonding in the octahedra between $NH_4^+$ and $BF_4^-$.

FIGS. 6A-C Different kinds of $(NH_4)(BF_4)_6$ octahedra within each structure, (a) (DH)$(NH_4)(BF_4)_3$, (b) (DF)$(NH_4)(BF_4)_3$, (c) (DCl)$(NH_4)(BF_4)_3$.

FIG. 8a illustrates the $(NH_4)(BF_4)_6$ octahedra in structure $(DH)(NH_4)(BF_4)_3$, in accordance with one embodiment of the invention.

DETAILED DESCRIPTION

Figure 1A:
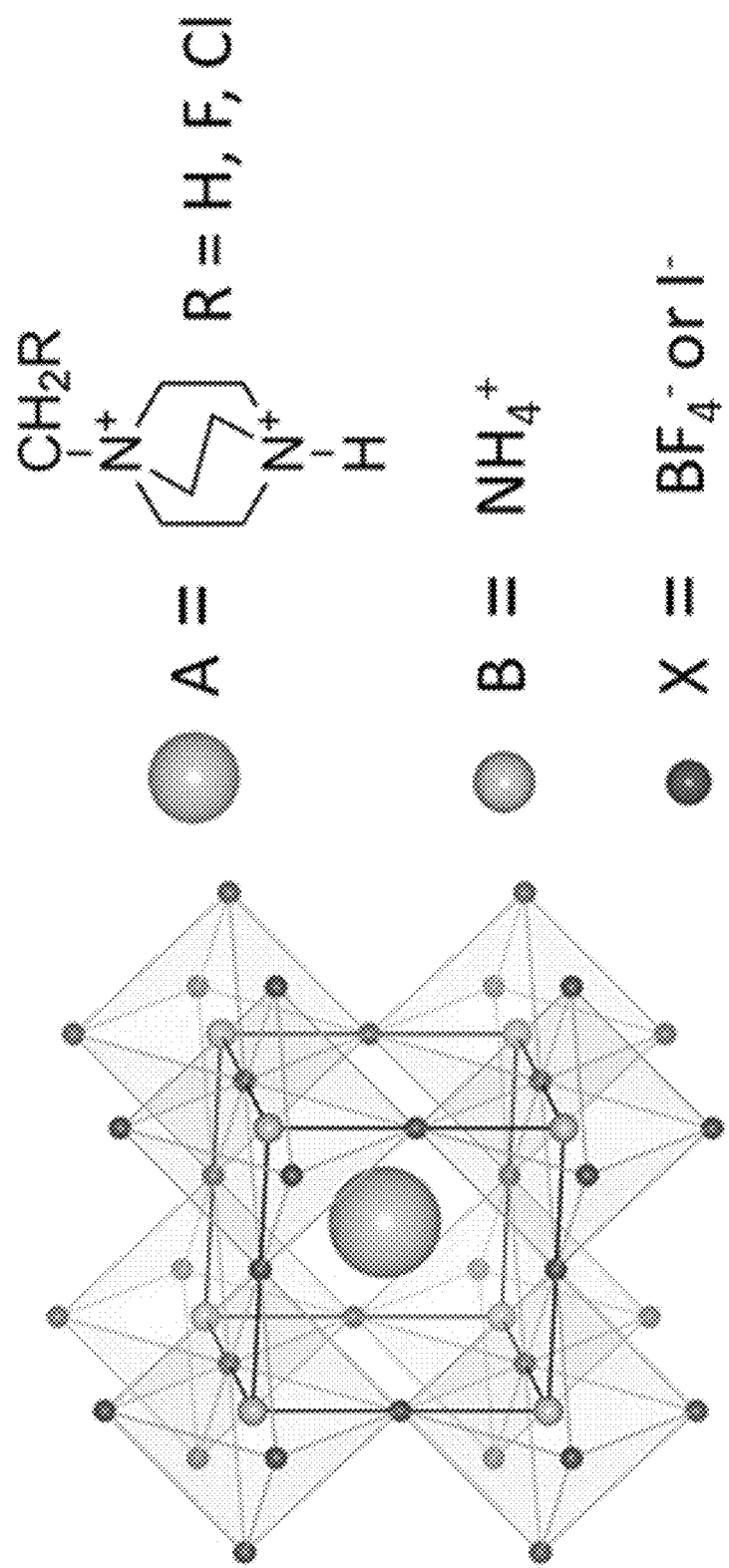
FIG. 1A illustrates a general perovskite crystal framework (left side), as well as the series of organic perovskites that were synthesized and investigated in the present disclosure (right side)
Figure 2B:
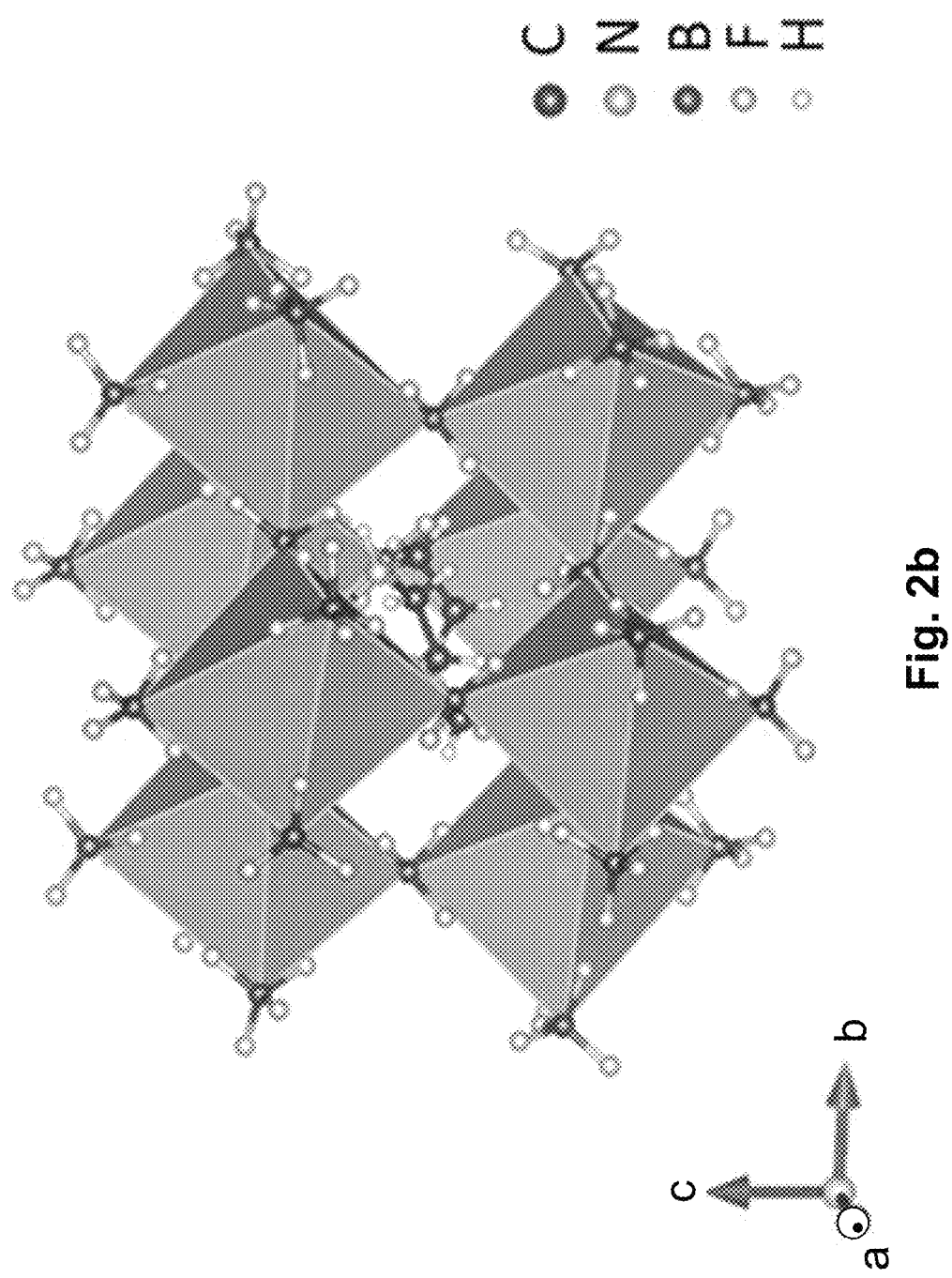
Figure 2C:
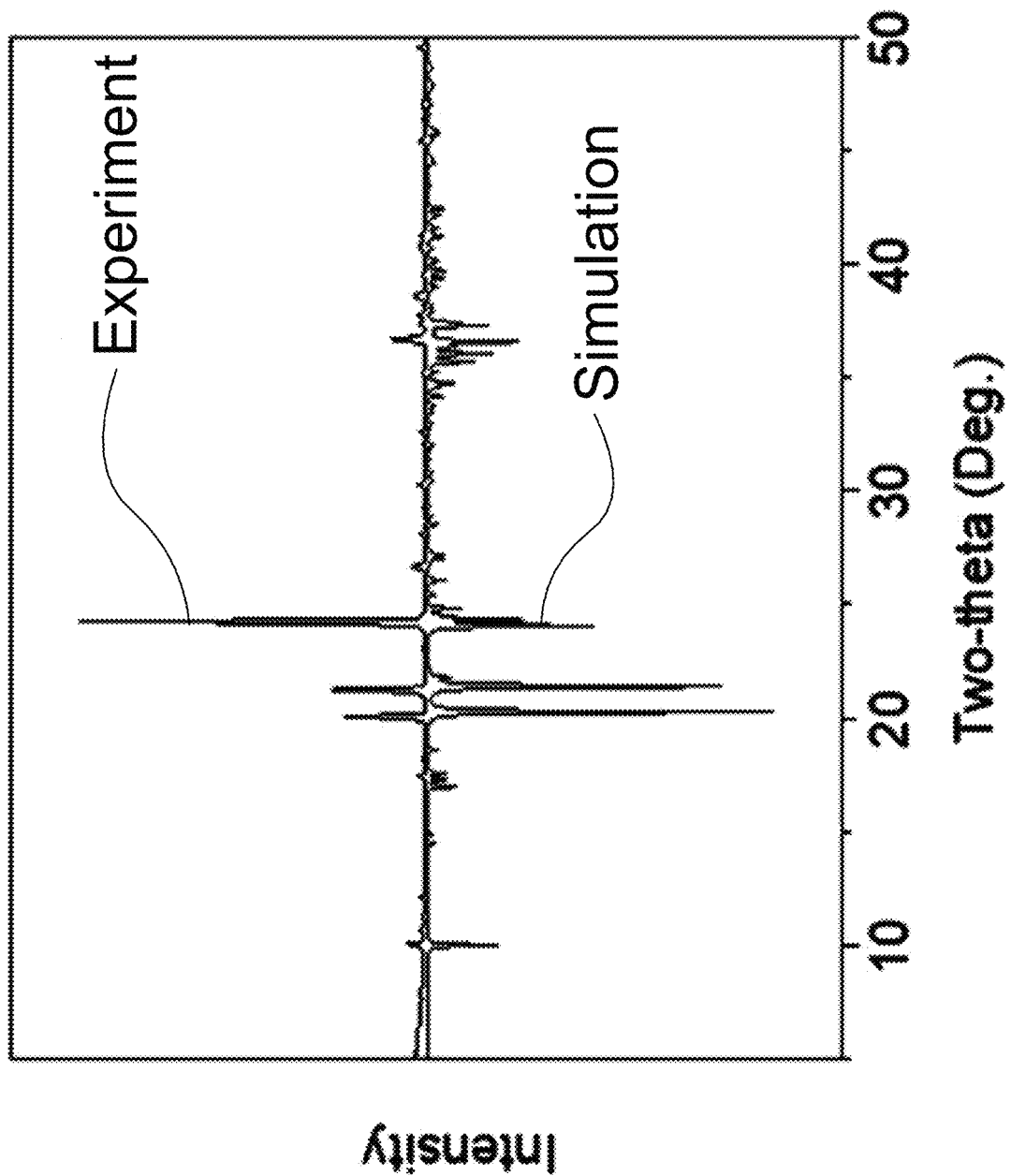
Figure 3A:
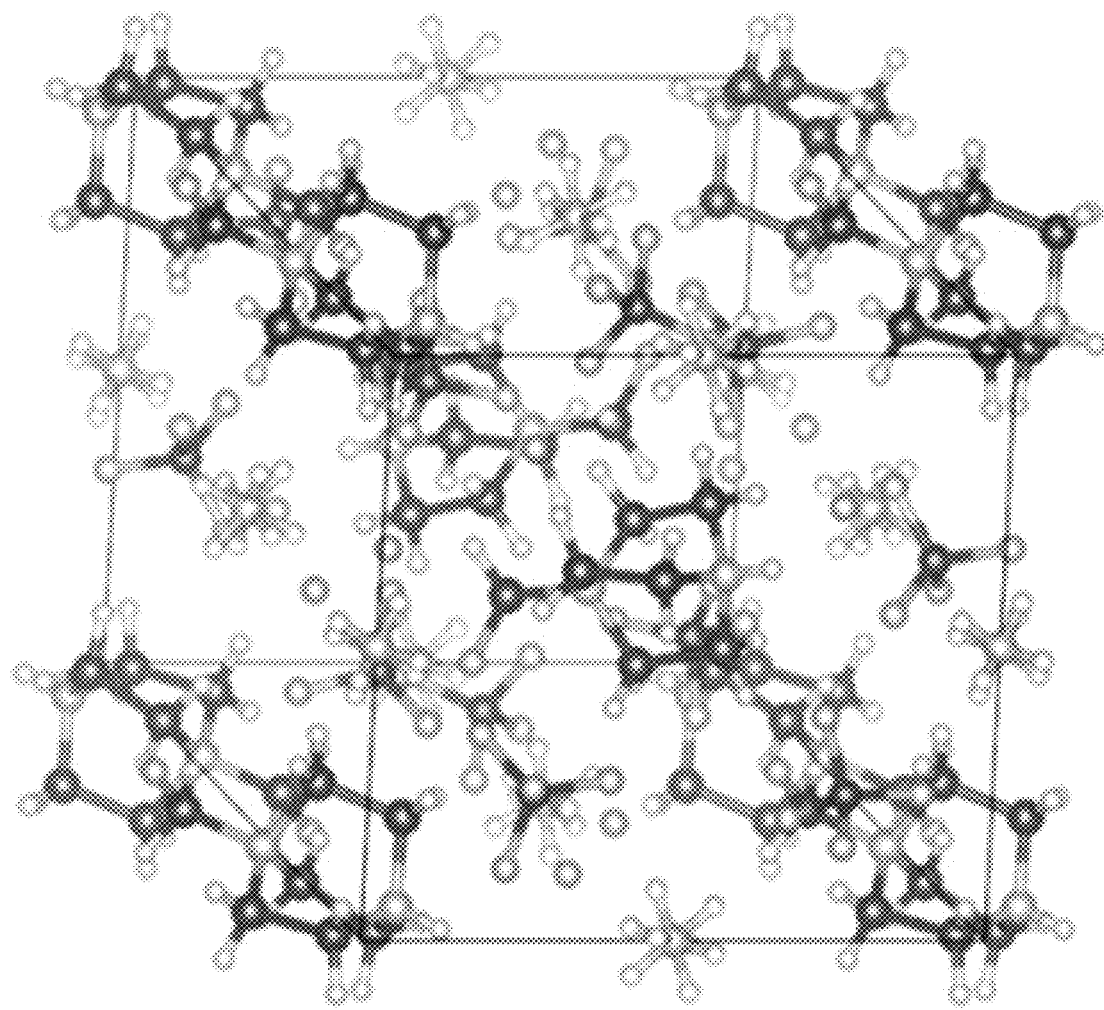
FIGS. 3A-C illustrate a unit cell, 3D crystal packing, and an x-ray diffraction (XRD) spectrum of (DF)$(NH_4)(BF_4)_3$, in accordance with one embodiment of the invention.
Figure 3A:
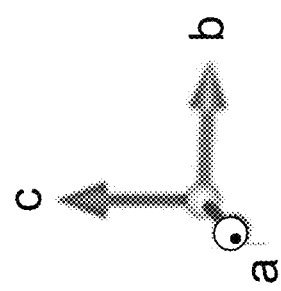
Figure 3B:
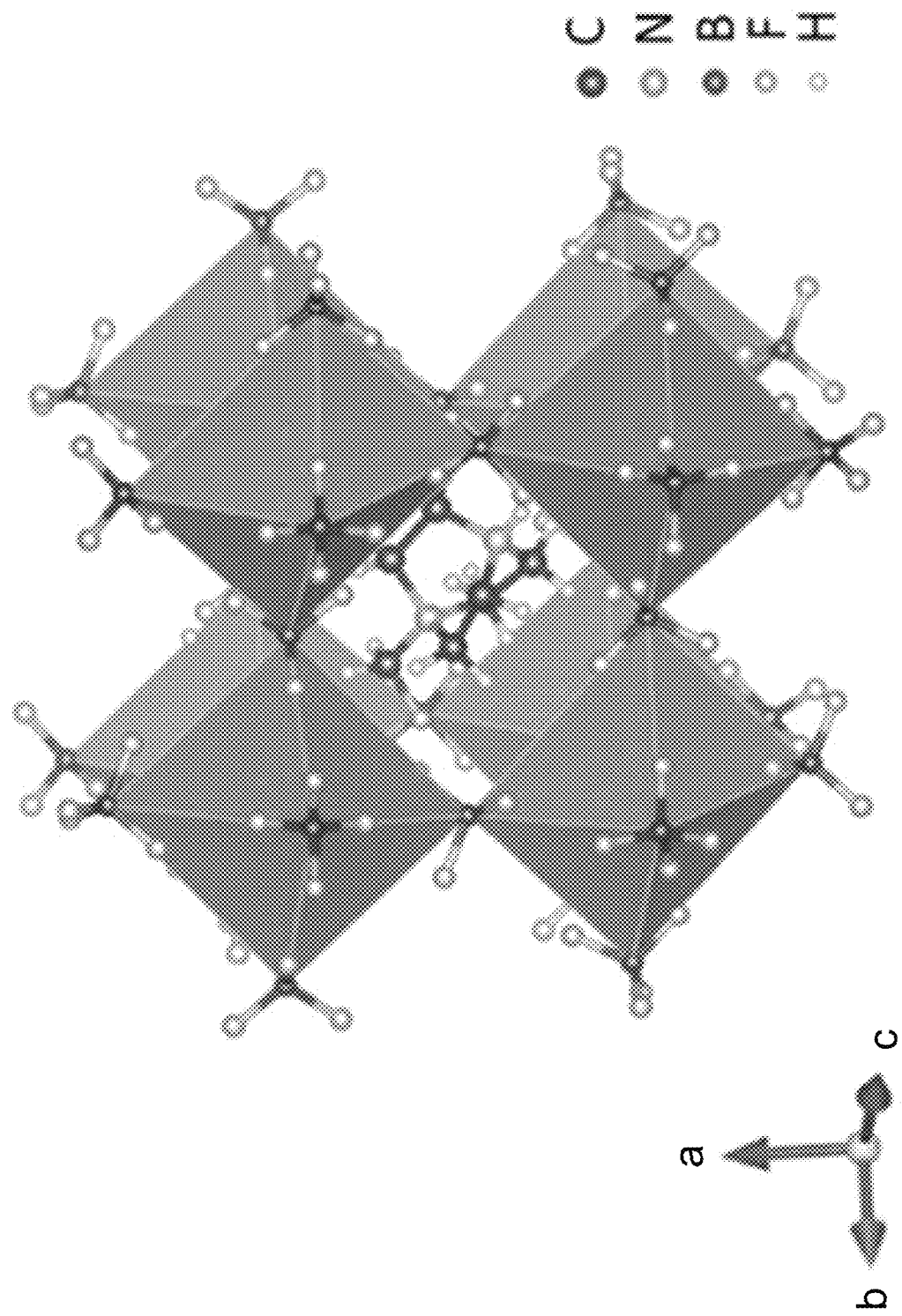
Figure 3C:
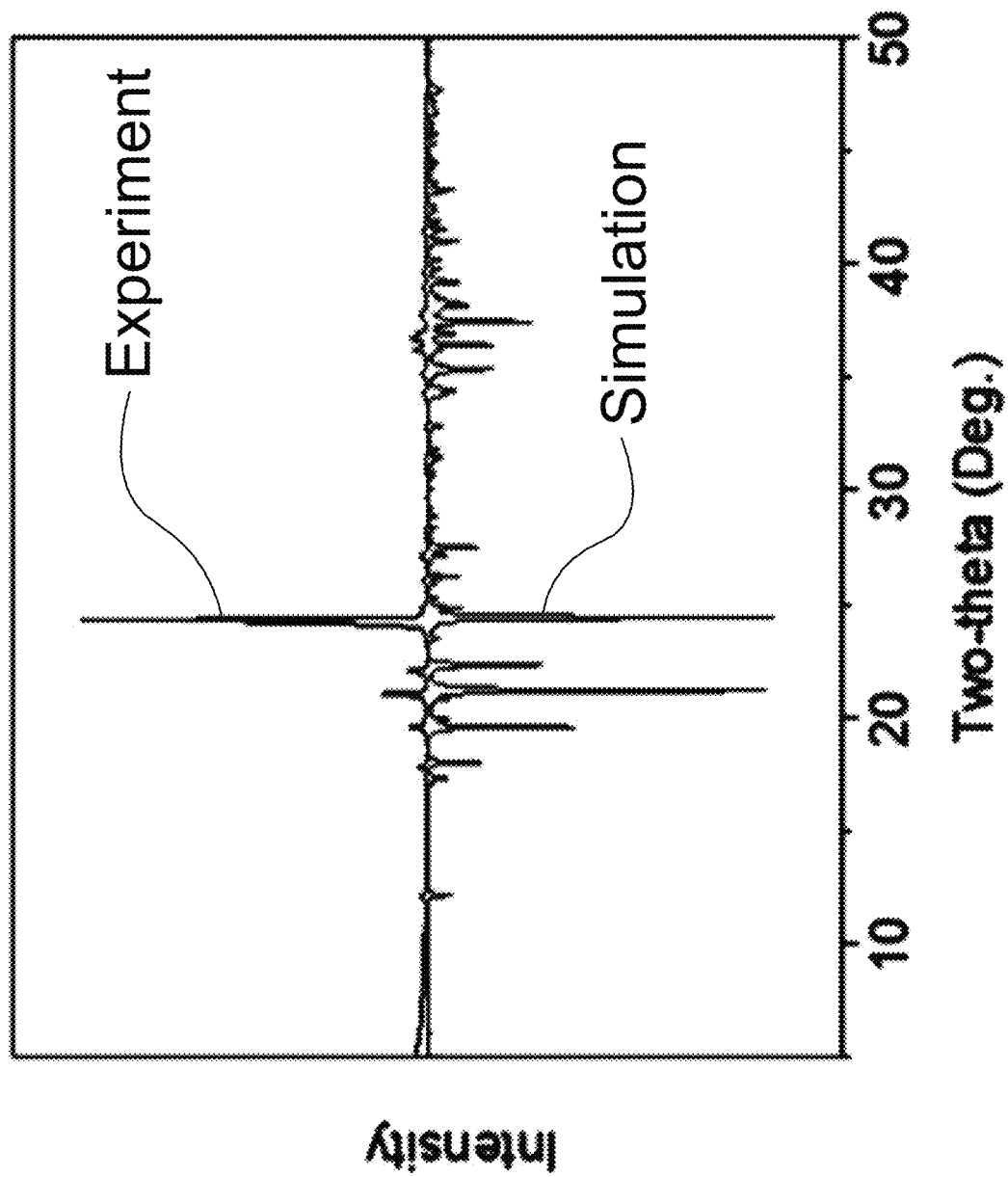
Figure 4A:
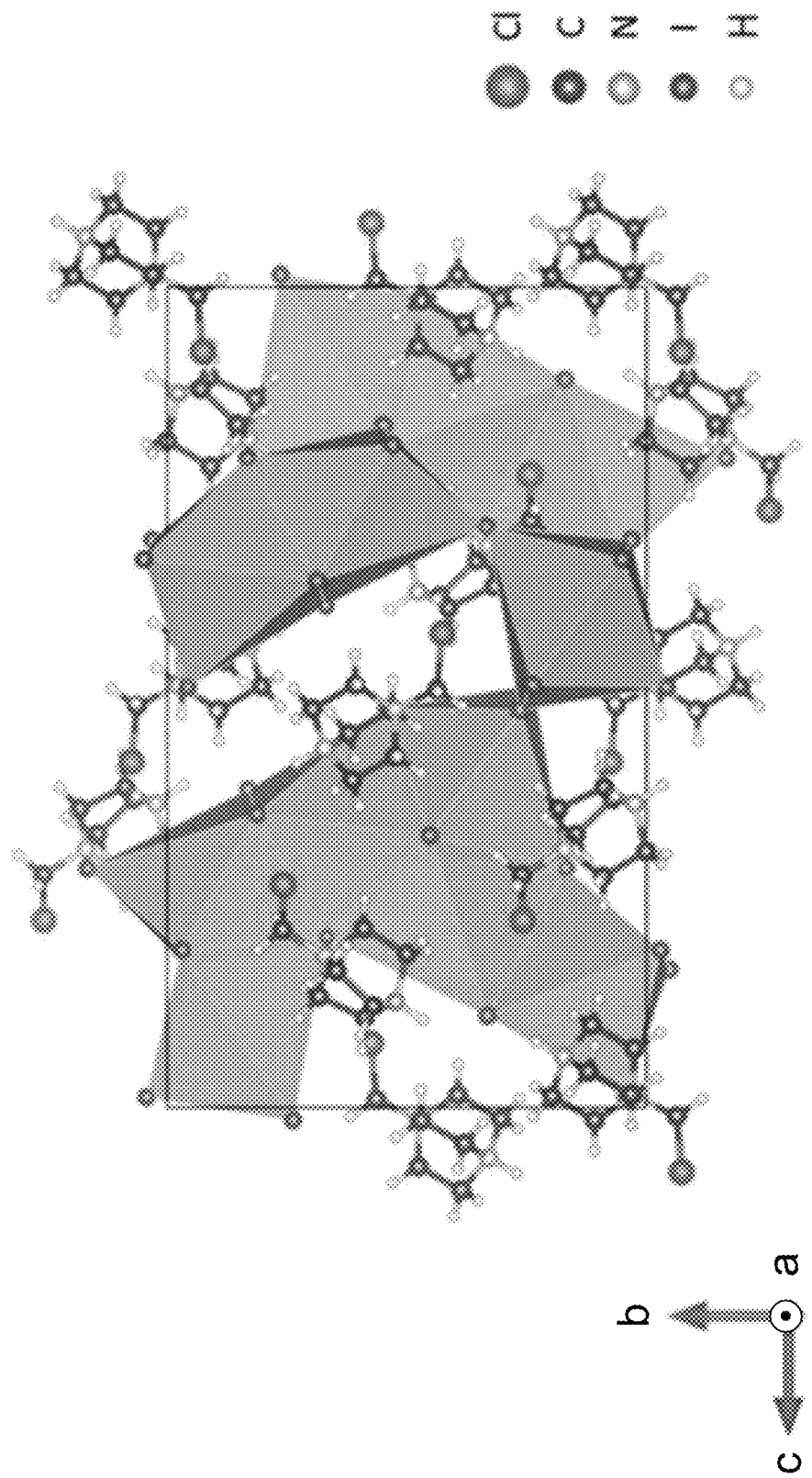
FIGS. 4A and B illustrate the structure and an x-ray diffraction (XRD) spectrum of $(DCl)_2(NH_4)_3(I)_7$.
Figure 4B:
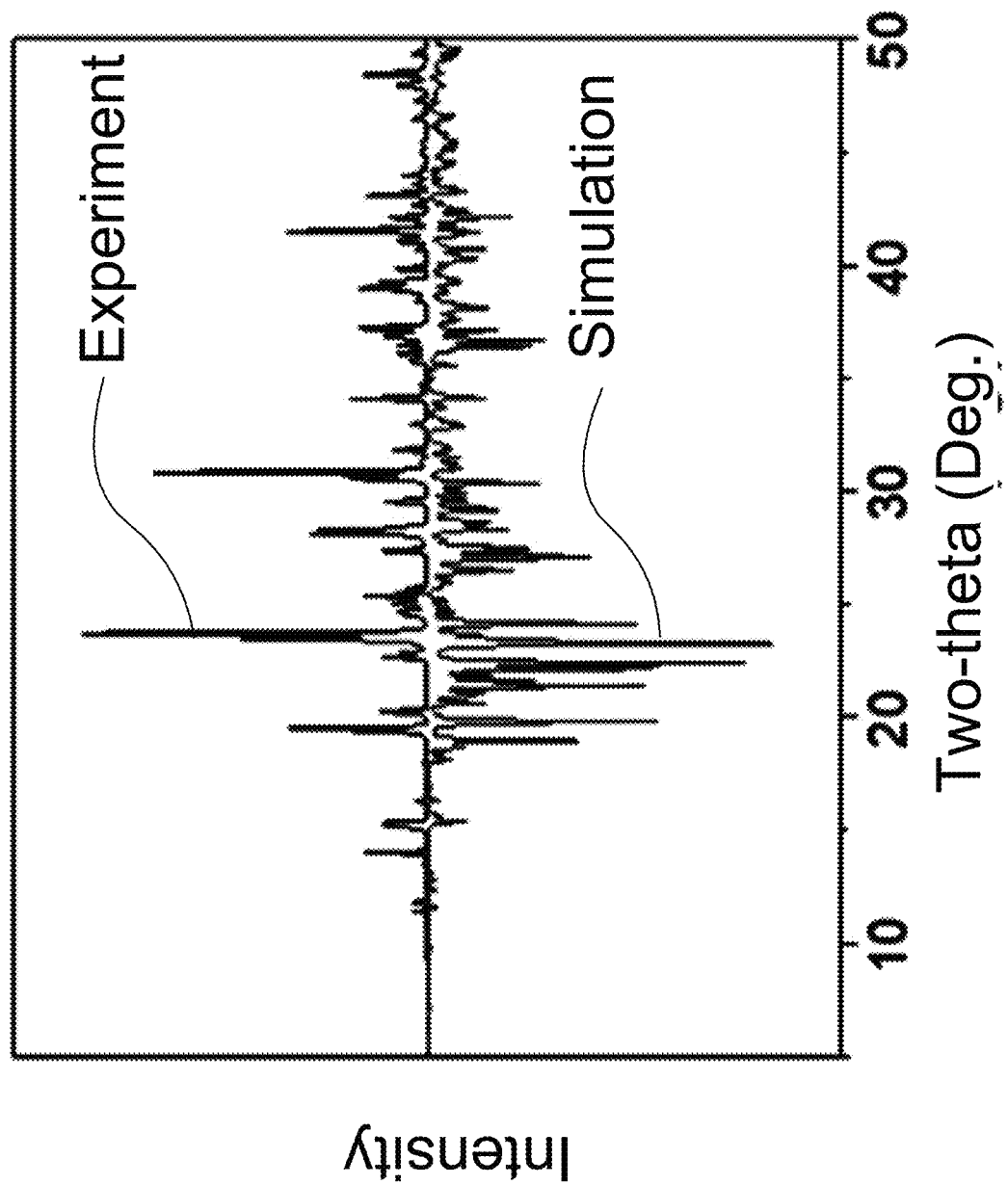

Organic perovskites with the general formula $ABX_3$ (in which the A and B sites are occupied by organic cations and the X site is a monovalent non-metallic counterion) have shown noncentrosymmetry induced by the A-site molecule where a functional group on the A-site molecule induces an asymmetry.

The 3D network of organic perovskites is composed of corner-sharing $BX_6$ octahedra connected via noncovalent interactions with the A site occupying the octahedral cavities (Ref. 7). This materials system offers a means to construct noncentrosymmetric structures by molecular engineering of organic components.

The present invention relates to a new class of 3D organic (i.e., metal-free) perovskites where highly polarizable functional groups are incorporated into the A-site molecule. To enable fitting the large functional group in the perovskite scaffold, a larger X site species is used to increase the size of the A-site. The dipole moment of the resulting perovskite materials can be optimized by increasing the size of the functional group on the A site molecule.

The increased polarizability of the A-site molecule and the resulting organic perovskite material is demonstrated by the high electrooptic coefficient achieved by the resulting materials. Accordingly, the present invention relates the construction of stable, noncentrosymmetric EO-active organic perovskite materials through the selection of suitable A, B and X constituents.

Spontaneous polarization ($P_s$)—a key consideration for determining the strength of the EO effect—depends on the dipole moment of the A site and its alignment in the cavity of the $BX_6$ frameworks (Ref 10). Additionally, the noncovalent interactions between the A- and X-site constituents distort the $BX_6$ octahedra and induce structural asymmetry, resulting in polarization. As a result, increasing the dipole moment of the A-site cation is a path towards increasing the total polarization in the crystal. This can be done by engineering the A-site cation with polarizable functional groups.

As the size of the cavity of the $BX_6$ framework is finite, only certain sizes of A-site cations can fit in the 3D perovskite scaffold.

In accordance with an embodiment of the present invention, a new class of organic perovskites is provided which overcomes the collapse of the 3D perovskite structure upon the addition of large A-site molecules.

The 3D organic perovskites of the present invention are solution-processed materials that can be readily integrated with silicon photonics. These organic perovskite systems are also very stable and can maintain their polarization over time. These 3D organic perovskites are suitable for use in on-chip modulators, electro-optic devices, piezoelectric devices, or silicon photonics devices.

In one embodiment, the present invention provides 3D organic perovskites having the Formula (I) $ABX_3$, wherein A has the formula $DR^{2+}$, wherein $DR^{2+}$ is:

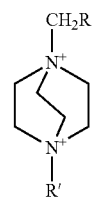

wherein R is F, Cl, Br, CN, or OH; and R' is H or $CH_3$; B is $NH_4^+$; and X is $BF_4^-$ or $PF_6^-$.

EO modulation has been observed in an organic perovskite: $(DH)NH_4I_3$, D=N-methyl-N'-diazabicyclo[2.2.2]octonium (Ref 9). This material had N-methyl-N'-diazabicyclo[2.2.2]octonium in the A-site, and this resulted in the noncentrosymmetry of the crystal.

To evaluate the performance of the organic perovskite materials, a series of organic perovskites employing the A-site cation $DR^{2+}$ (D=N-methyl-N'-diazabicyclo[2.2.2]octonium, R=H, F, Cl) were synthesized. In preferred embodiments of the present invention, one hydrogen atom on the N-methyl group was replaced with a larger, more polarizable halogen atom. The larger polarizability of the halogen atoms on the A-site cation can be expected to increase the molecular dipole strength.

FIG. 1A illustrates a general perovskite crystal framework (left side), as well as the series of organic perovskites that were synthesized and investigated in the present disclosure (right side).

A series of three new 3D organic perovskites of the general formula of $(DR)(NH_4)(BF_4)_3$ were synthesized, wherein $BF_4^-$ was employed as the X-site counterion, and R is H, F or Cl. FIG. 1C illustrates this series of perovskite structured crystals wherein R in the A-site cation is H (left), F (middle) and Cl (right).

FIG. 1B illustrates a series of three organic perovskite structured crystals in which the X sites are occupied by $I^-$ ions and R=H (left), F (middle) and Cl (right). When F is used as the X-site, the perovskite structure collapses when R in the A-site cation is Cl.

To prevent the collapse of the 3D framework for larger A-site cations, $BF_4^-$ is used instead of $I^-$ as the X site, in accordance with the present invention.

The large radius of $BF_4^-$ (232 pm) stabilizes the 3D structure for the highly polarizable Cl-substituted cation. Because the radius of a $BF_4^-$ anion is larger than that of an I⁻ anion, the volume of a resulting $BX_6$ cage is large enough to accommodate the Cl, without compromising a crystal's stability.

Each cation is isolated in $BX_6$ cages, which limits dipole-dipole interactions and so avoids the formation of centrosymmetric crystal packing present in other organic EO modulator materials.

The structural dimension evolution is in good agreement with the Goldschmidt's Tolerance Factor, namely $$(R_A+R_X)=t\sqrt{2}(R_B+R_X)$$

where $R_A$, $R_B$, and $R_X$ are the ionic radii for the corresponding ions and the tolerance factor must satisfy t≈1 (Ref. 12). For most 3D perovskites, it is found that $0.8 \leq t \leq 1.0$.

Table 1 shows the Goldschmidt tolerance factors of six organic perovskite crystals. The effective diameter of a $DR^{2+}$ cation can be defined as the distance between two atoms that are furthest apart, based on the single crystal structures.

TABLE 1

|  | $DH^{2+}$ (268 pm) | $DF^{2+}$ (274 pm) | $DCl^{2+}$ (299 pm) |
|---|---|---|---|
| I⁻ (220 pm) | 0.98 | 0.99 | 1.04 |
| $BF_4^-$ (232 pm) | 0.97 | 0.98 | 1.01 |

EXAMPLES

Example 1: Synthetic Methods

Synthesis of the A-site cation: $DR^{2+}$ (R=H, F, Cl) cations were synthesized and characterized according to the methods disclosed by WO2014/68341, which is incorporated herein by reference in its entirety (Ref. 16). Briefly, N—N'-diazabicyclo[2.2.2]octonium and methyl iodide were dissolved in acetone in a 1:1.1 mole ratio at room temperature, then the mixed solution was stabilized in the dark for 48 h. The resulting precipitate was collected by filtration and washed with a large amount of diethyl ether to afford high-yield (DH)I as transparent crystals. (DF)I and (DCl)Cl were prepared using the similar method by reacting N—N'-diazabicyclo[2.2.2]octonium with fluoroiodomethane and dichoromethane, respectively.

Synthesis of the organic perovskites: Each of the crystals displayed in FIGS. 1A-C was prepared in an aqueous solution through a step-cooling method.

The 3D $(DR)(NH_4)(BF_4)_3$ crystals were prepared by adopting the step-cooling method by mixing stoichiometric amounts of DR and $NH_4BF_4$ in excess $HBF_4$ aqueous solution in a 20 ml vial. The mixture was dissolved by heating it up to 80□ for 1 h. The clear solution was then cooled to room temperature at a rate of 4 K/h to yield centimeter-sized transparent crystals. The crystals of counterparts were prepared in a similar way, by using HI solution instead of $HBF_4$ aqueous solution.

Example 2: X-Ray Crystallography

Single-crystal X-ray analysis: The structures of the organic perovskites were determined by powder- and single-crystal X-ray diffraction. Depictions of the crystal structures are shown in FIGS. 2A-C, 3A-C, 4A-B and FIGS. 5A-E)

Single crystal structures were measured with Bruker Kappa APEX-DUO diffractometer equipped with a rotating anode with graphite-monochromated Mo-Kα radiation (Burker Triumph, λ=0.71073 Å). The structures were solved by SHLEXT and SHELXL-2016/6, respectively. The detailed crystal information is listed in Table 2.

TABLE 2

| Compound | $(DH)(NH_4)(BF_4)_3$ | $(DF)(NH_4)(BF_4)_3$ | $(DCl)(NH_4)(BF_4)_3$ | $(DCl)_2(NH_4)_3I_7$ |
|---|---|---|---|---|
| CCDC number | 2006695 | 2006696 | 2006697 | 2006698 |
| Formula | $C_7H_{20}B_3F_{12}N_3$ | $C_7H_{19}B_3F_{13}N_3$ | $C_7H_{19}B_3ClF_{12}N_3$ | $C_{14}H_{42}Cl_2I_7N_7$ |
| Formula weight | 406.69 | 424.68 | 441.13 | 1267.74 |
| Temperature | 200 K | 150 K | 150 K | 150 K |
| Crystal system | Monoclinic | Monoclinic | Triclinic | Orthorhombic |
| Space group | $P2_1$ | $P2_1/c$ | P1 | $P2_12_12_1$ |
| a (Å) | 9.9737 (3) | 14.7383 (6) | 7.3743 (3) | 9.6861 (3) |
| b (Å) | 10.8062 (4) | 10.2392 (4) | 15.0001 (7) | 14.4232 (4) |
| c (Å) | 14.5050 (5) | 10.4862 (4) | 15.0678 (7) | 24.7146 (7) |
| V (Å³) | 1563.31 (9) | 1567.54 (11) | 1653.49 | 3452.74 (17) |
| α (°) | 90 | 90 | 88.773 | 90 |
| β (°) | 90.118 | 97.874 | 84.993 | 90 |
| γ (°) | 90 | 90 | 84.842 | 90 |
| Z value | 4 | 4 | 4 | 4 |
| Density (mg/m³) | 1.728 | 1.800 | 1.772 | 2.439 |
| R1 (final) | 0.0397 | 0.0377 | 0.0529 | 0.0126 |
| wR2 (final) | 0.0956 | 0.0921 | 0.1385 | 0.0285 |
| R1 (all) | 0.0496 | 0.0480 | 0.0551 | 0.0129 |
| wR2 (all) | 0.1001 | 0.0968 | 0.1413 | 0.0286 |

As seen in FIG. 5A, $(DCl)(NH_4)(BF_4)_3$ displays a typical 3D perovskite structure, composed of a corner-sharing network of $(NH_4)(BF_4)_6$ octahedra with a $DCl^{2+}$ cation 510 occupying the octahedral cavities and maintaining the electroneutrality of the 3D perovskite structure 505. All components are held together by hydrogen and halogen bonds. The $DCl^{2+}$ is closely linked to the $(NH_4)(BF_4)_6$ octahedra via C—H • • • F hydrogen bonds 515 (2.31-2.60 Å, dotted line) and C—Cl • • • F heterohalogen • • • halogen interactions 520 (3.72 Å, dotted line), which align the cation in each cavity (FIG. 5B). The octahedron formed between $NH_4^+$ 555 and $BF_4^-$ 560 by N—H • • • F hydrogen bonds (2.19-2.58 Å, dotted line) shows a distorted geometry (FIG. 5C). The noncovalent bonding decreases the rigidity of the octahedra, facilitating a distortion large enough to allow the $DCl^{2+}$ to fit inside the perovskite cavity (FIGS. 6A-C and Table 3) (Ref. 13). The degree of the distortion in $(DCl)(NH_4)(BF_4)_3$ is an order of magnitude larger than in the H and F counterparts, which is attributed to the size of $DCl^{2+}$ cation.

Figure 5D:
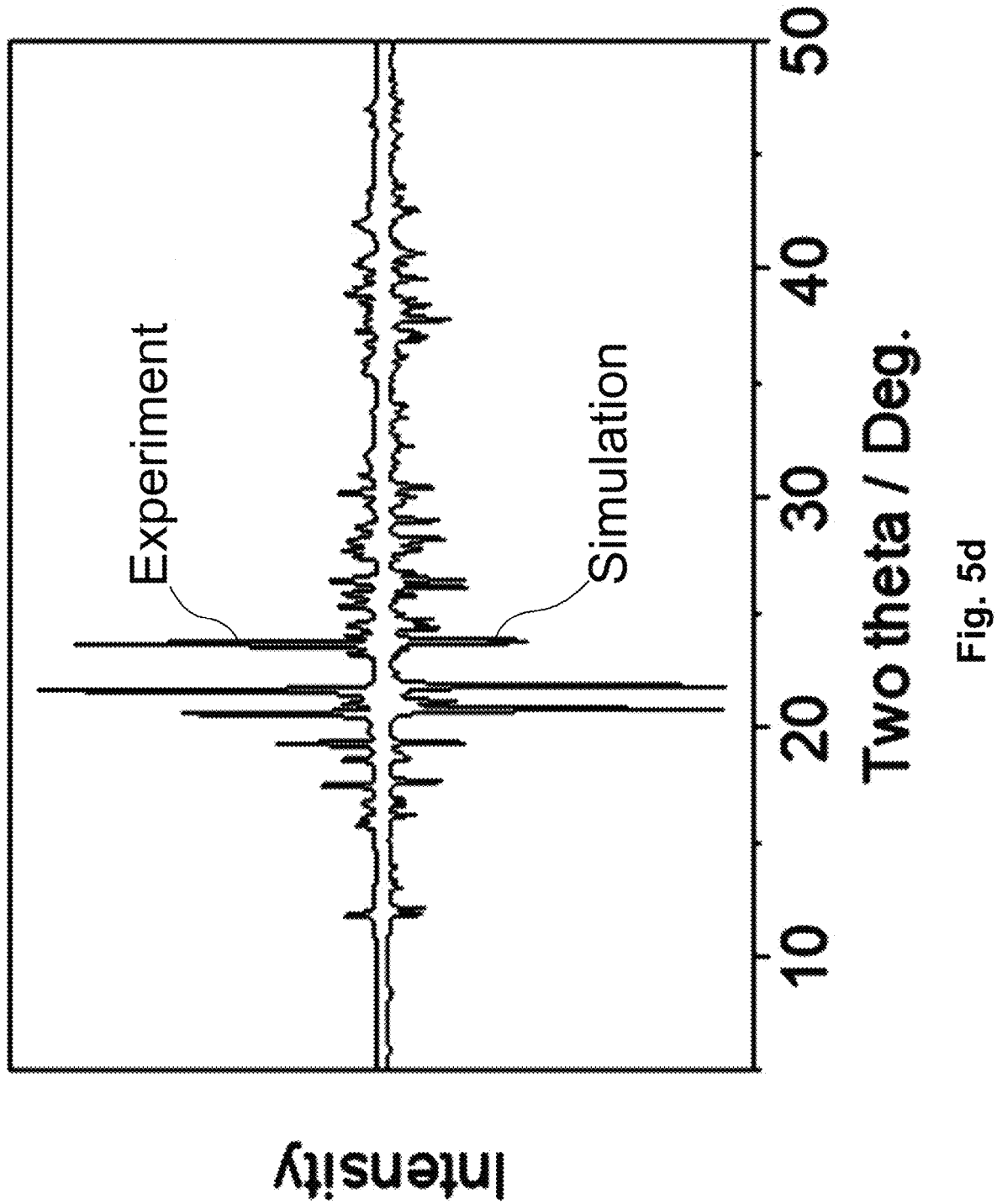
FIG. 5d is a graph showing experimental and simulated powder X-ray diffraction spectra, of (DCl)$(NH_4)(BF_4)_3$, in accordance with one embodiment of the invention.
Figure 6A:
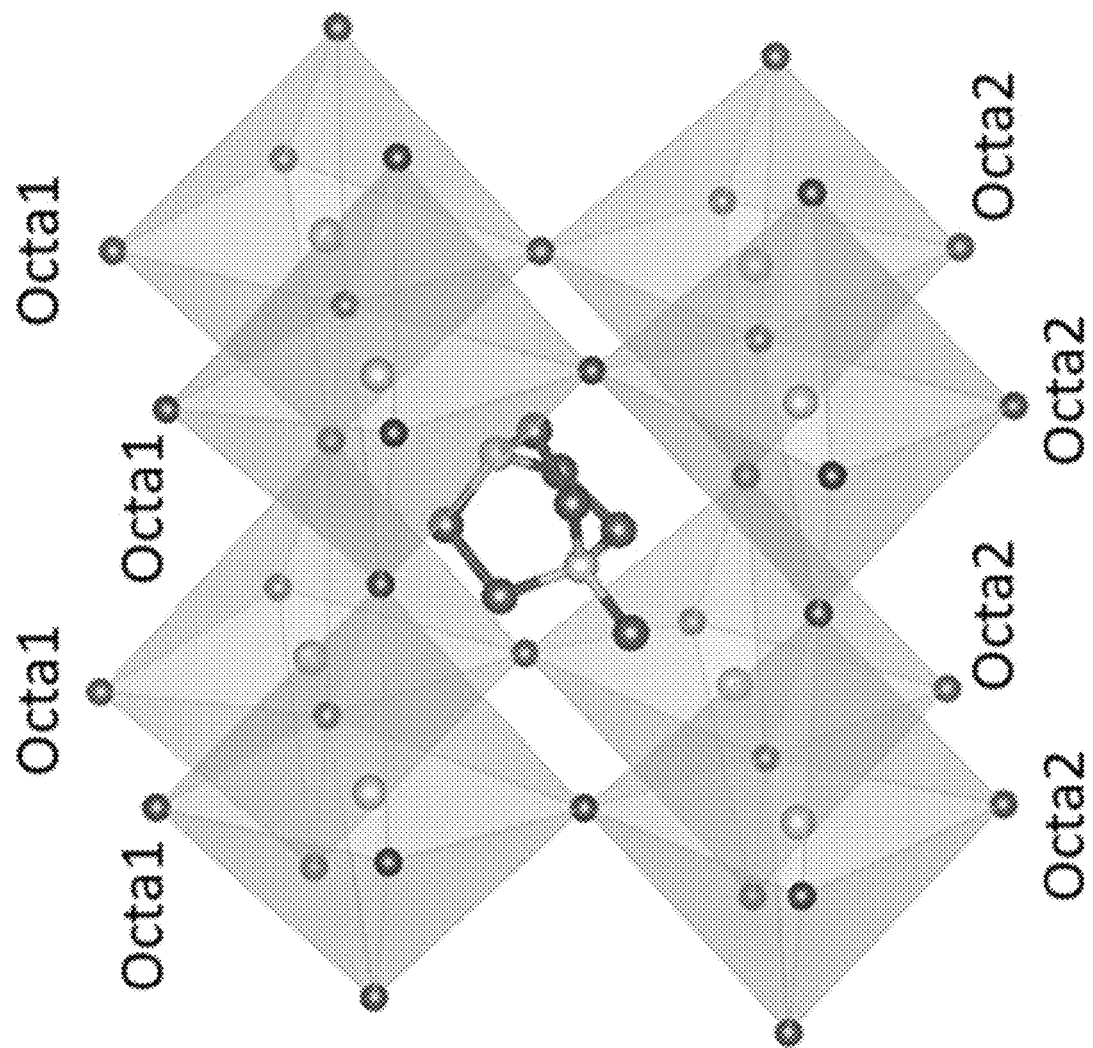
Figure 6B:
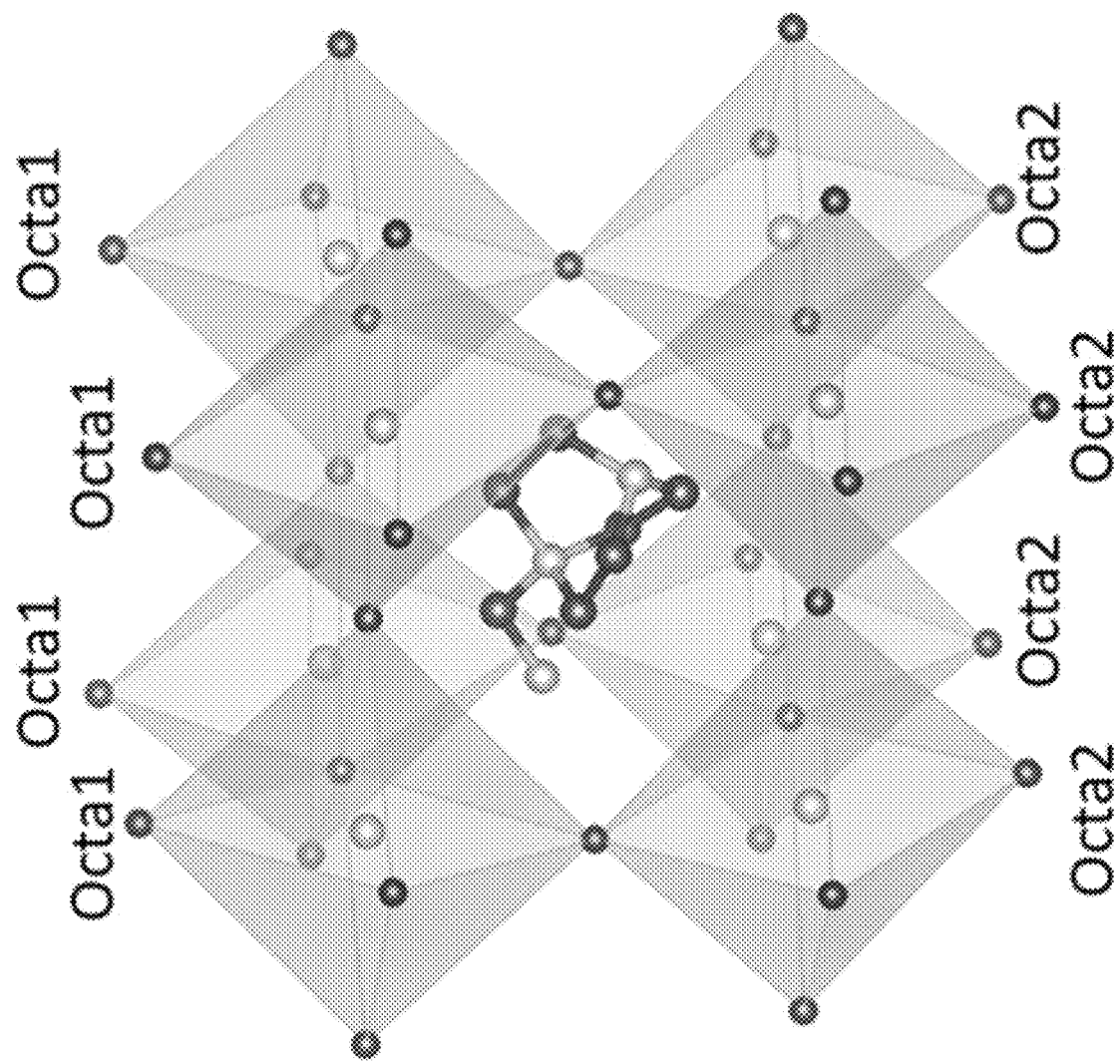

The phase purity was also investigated with powder X-ray diffraction: the experimental (upper trace) and simulated (lower trace) powder X-ray diffraction were well-matched, which confirms that the crystal is in a single phase (FIG. 5D).

Figure 5E:
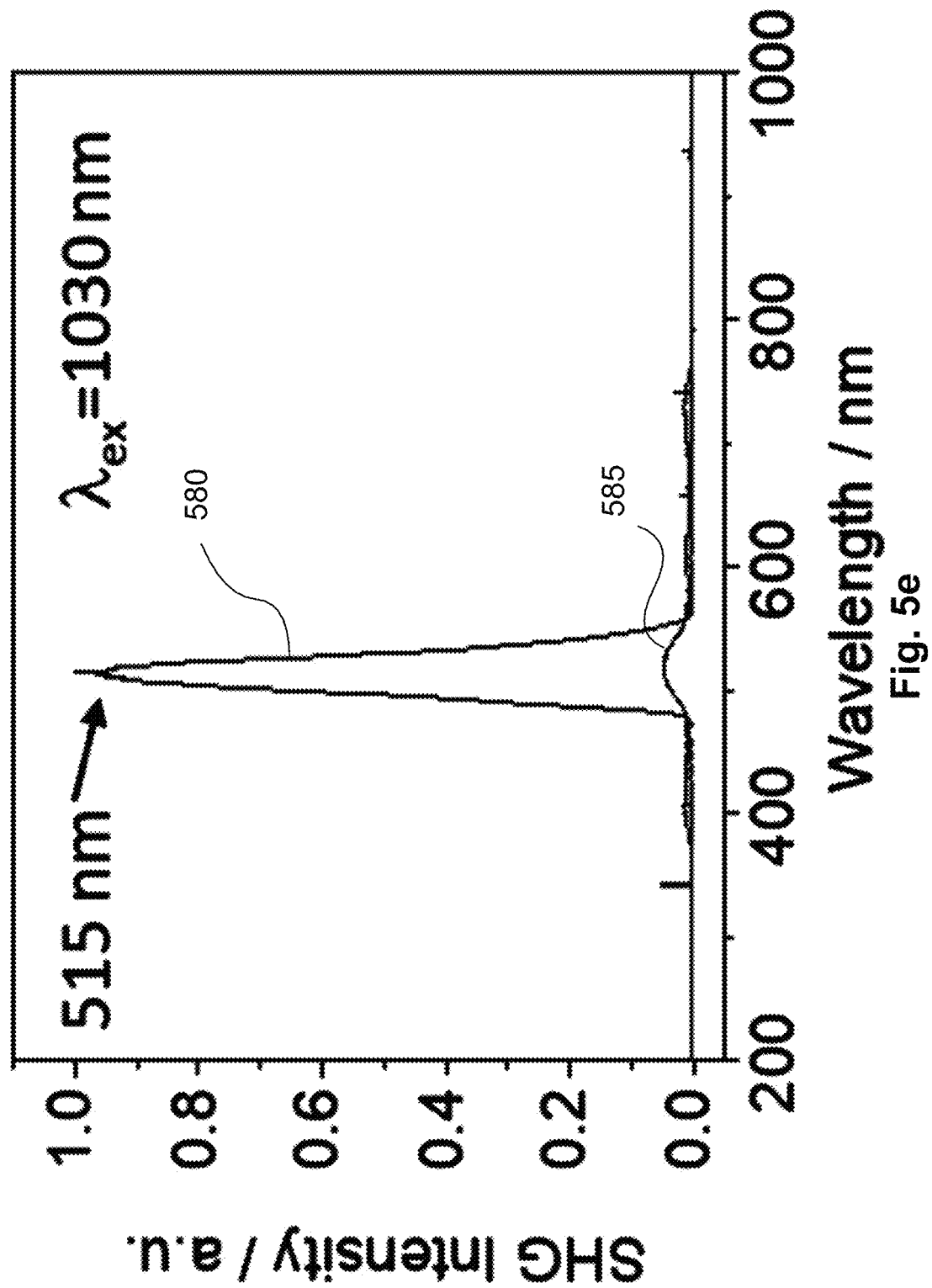
FIG. 5e is a spectrum of second harmonic generation intensity caused by 1030 nm laser pulse illumination of (DCl)$(NH_4)(BF_4)_3$ and $(DCl)_2(NH_4)_3I_7$.

Strong second harmonic generation (SHG) signal for $(DCl)(NH_4)(BF_4)_3$ (580) was observed at room temperature when the crystal powder was illuminated with a 1030 nm femtosecond laser, confirming the noncentrosymmetric structure of the crystal and its propensity for second-order optical nonlinearity (FIG. 5E). Under the same experimental conditions, the SHG intensity of $(DCl)_2(NH_4)_3I_7$ (585) was several orders of magnitude lower. As SHG is primarily a result of the polarized electrons in the material, it can be concluded that the polarization is significantly stronger in the $(DCl)(NH_4)(BF_4)_3$ materials compared to their $I^-$ counterpart.

The $(NH_4)(BF_4)_6$ octahedra in crystals according to embodiments can be distorted with a distortion that can be calculated according to the following equation:

$$\Delta d = \left(\frac{1}{6}\right)\Sigma\left(\frac{d_n - d}{d}\right)^2$$

where d is the mean N ••• B distance and $d_n$ are the six N ••• B individual distances.

Table 3 summarizes the distortions of individual octahedra with crystal structures.

TABLE 3

|  | $\Delta d_1$ ($\times 10^{-4}$) | $\Delta d_2$ ($\times 10^{-4}$) | $\Delta d_3$ ($\times 10^{-4}$) | $\Delta d_4$ ($\times 10^{-4}$) | $\Delta d_{avg}$ ($\times 10^{-4}$) |
|---|---|---|---|---|---|
| $(DH)(NH_4)(BF_4)_3$ | 1.850 | 0.684 | | | 1.267 |
| $(DF)(NH_4)(BF_4)_3$ | 1.420 | 4.021 | | | 2.721 |
| $(DCl)(NH_4)(BF_4)_3$ | 33.44 | 32.83 | 32.42 | 12.17 | 27.47 |

Example 4: Density Functional Theory

The molecular dipole moments of $DR^{2+}$ cations were calculated by DFT calculation carried out in Gaussian09 package using the B3LYP functional. The electronic structures were optimized using 6-31G basis set. The crystal polarization calculations have been performed in the framework of DFT (Ref. 17) with Perdew-Burke-Ernzerhof generalized gradient approximation (Ref. 18) (GGA-PBE) for the exchange-correlation functional and GTH pseudopotentials (Ref. 19). Van der Waals correction is considered for all calculations at a DFT-D3 level (Ref. 20). The polarization calculations were performed using CP2K (Ref 21). An energy cutoff of 600 Ry was set for Gaussian basis sets with auxiliary planewave method. Geometry optimization was performed under BFGS algorithm. Berry phase approach was utilized to calculate system electric polarization (Ref. 22).

Figure 7A:
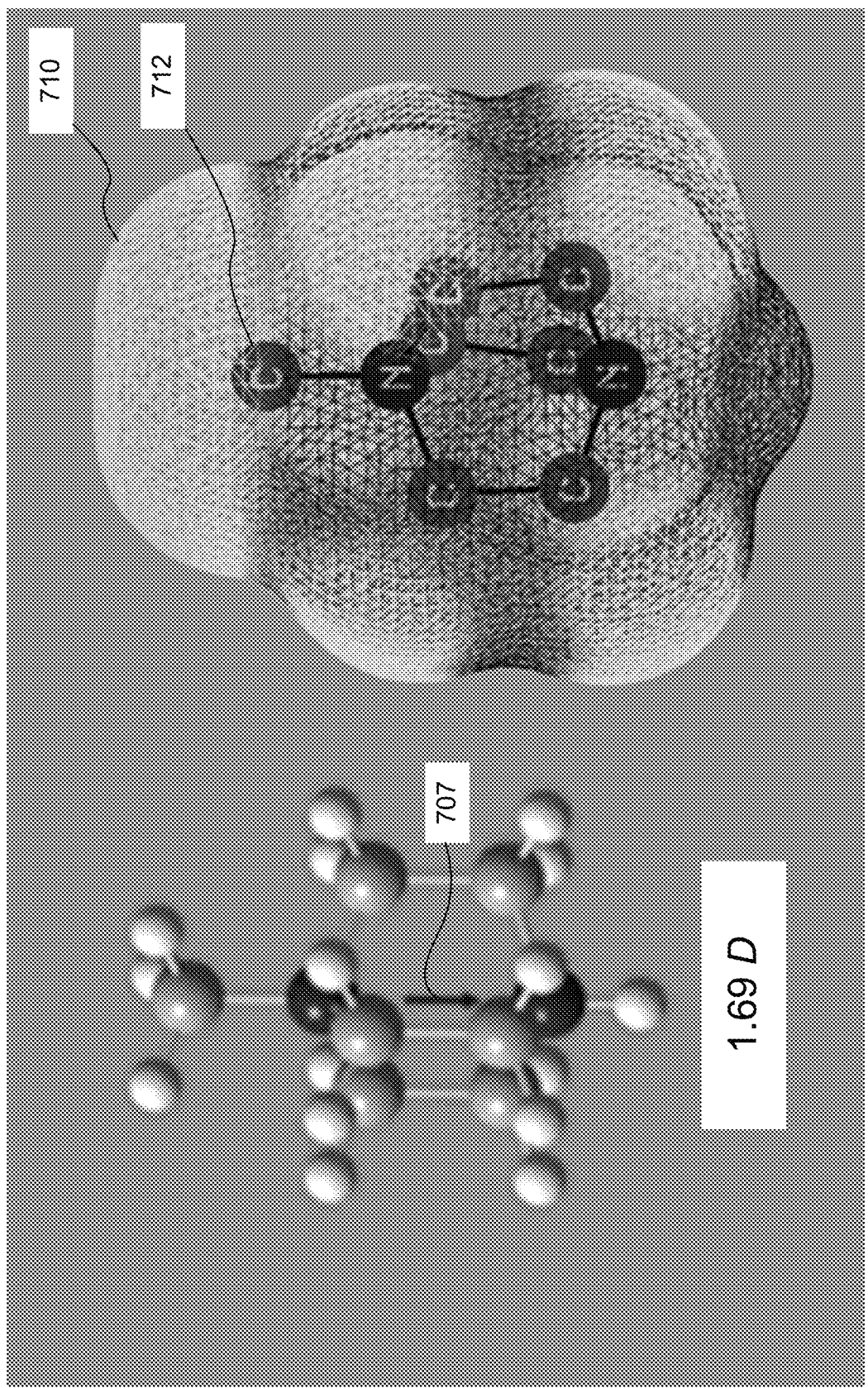
FIGS. 7A-C illustrate the molecular dipole moments and electrostatic potential mapping of three $DR^{2+}$ cations ((a), R=H; (b), R=F; (c), R=Cl).
Figure 7B:
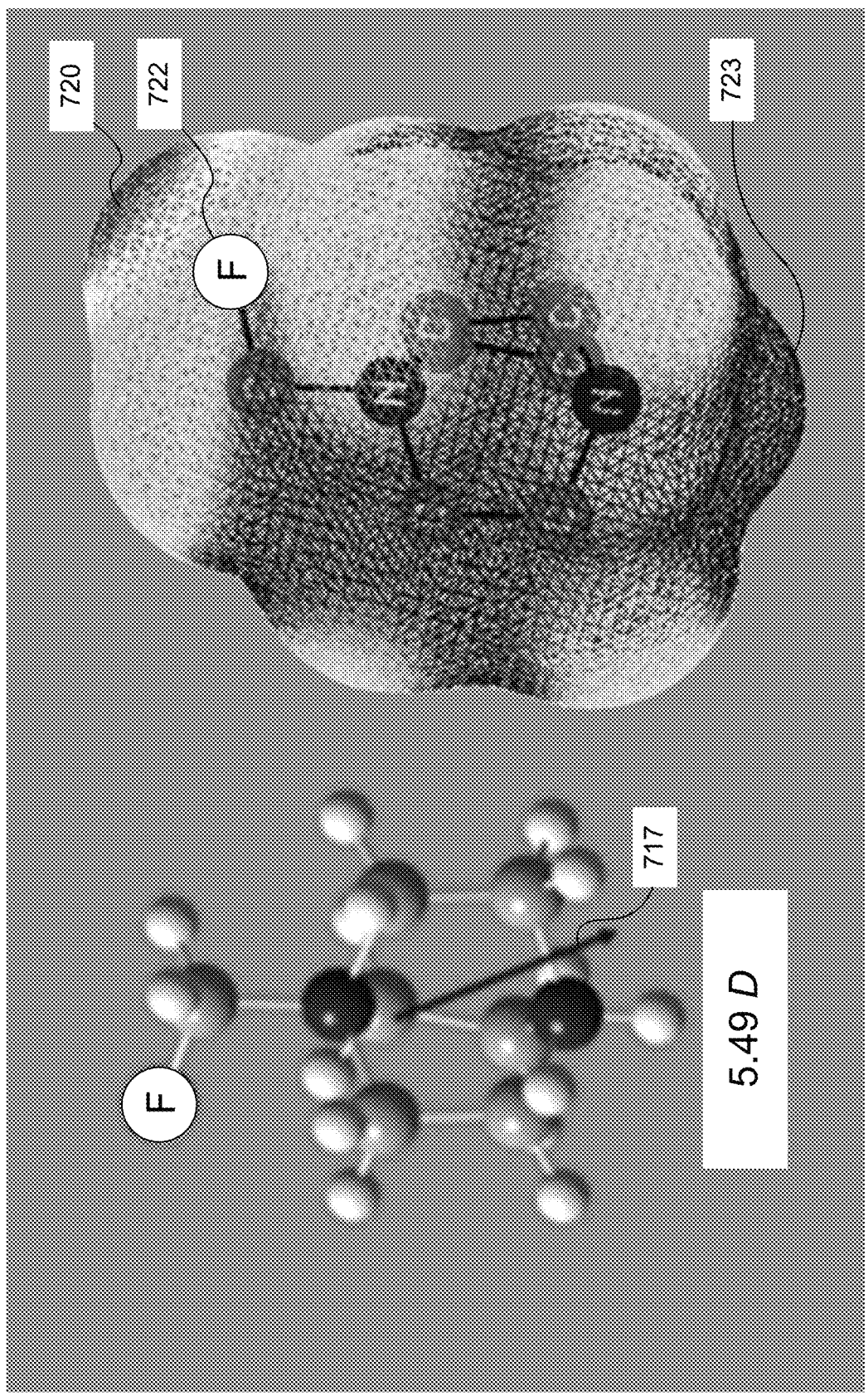
Figure 7C:
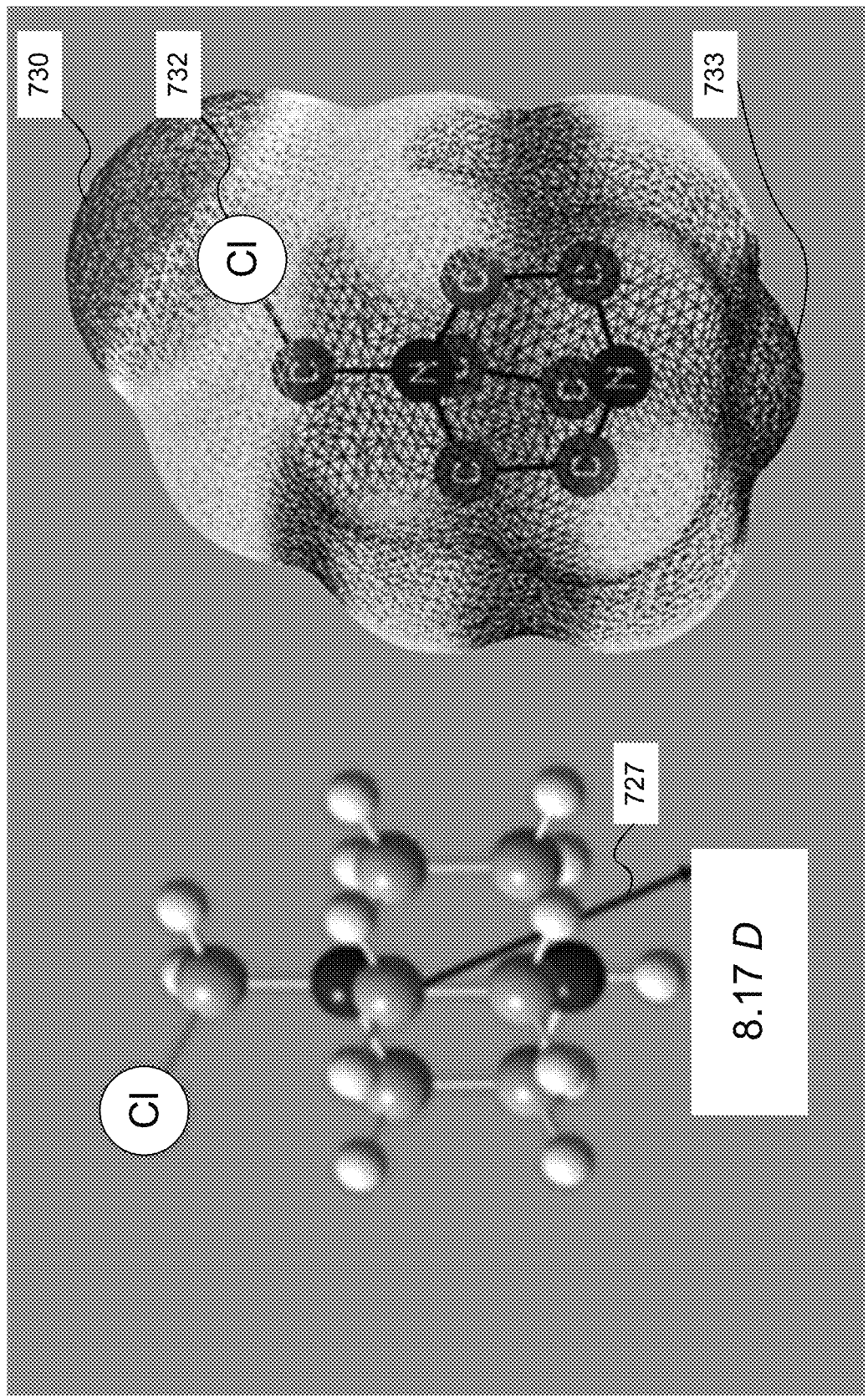

Density functional theory (DFT) was used to investigate the macroscopic polarization $P_s$ in the OP crystals. The $P_s$ depends primarily on the dipole ordering of the A-sites (Refs. 8, 10a). The molecular dipole moments and electrostatic potential maps of the A-site molecules were first calculated (FIGS. 7A-C). The dipole of $DH^{2+}$ has a strength of ~1.69 D and is oriented along the molecular trifold axis. This dipole originates from the reduction of the molecular symmetry through the attachment of the methyl group on the N—N'-diazabicyclo[2.2.2]octonium core.

FIG. 7A illustrates a $DH^{2+}$ cation, as can be enclosed in an A site of a perovskite crystal. DFT indicates the dipole moment of $DH^{2+}$ is approximately ~1.69 D and oriented approximately in the direction indicated by arrow 707 the molecular trifold axis. Electrostatic potential mapping of the molecule on the right side of FIG. 7A shows (−) charge distribution to be greater near the upper end 710 of the molecule, near the methyl group 712.

When one H atom on $DH^{2+}$ is replaced by a halogen atom (F and Cl), the dipole moments increase to 5.49 D for $DF^{2+}$ and 8.17 D for $DCl^{2+}$ (FIG. 7A-C, left). This increase is a direct consequence of the increased electronegativity of F and Cl. The increase in dipole moments is evident from the electrostatic potential mapping shown in FIG. 7A-C. The halogenation redistributes the electron density to make the rest of the molecule more positive and the halogen side electronegative. The $P_s$ of the three $(DR)(NH_4)(BF_4)_3$ crystals was calculated using the Berry phase polarization method based on the single crystal XRD data. It revealed that the electron redistribution leads to a dipole direction off-axis by ~15° with respect to the trifold axis of the N—N'-diazabicyclo[2.2.2]octonium core.

FIG. 7B illustrates a $DF^{2+}$ cation, as can be enclosed in an A site of a perovskite crystal according to an embodiment of the present invention. DFT indicates the dipole moment of $DF^{2+}$ is approximately ~5.49 D, and its direction as indicated by arrow 717 is approximately 15° with respect to the trifold axis of the N—N'-diazabicyclo[2.2.2]octonium core. Electrostatic potential mapping of the molecule on the right side of FIG. 7B shows (−) charge distribution to be greater near the upper end 720 of the molecule, near the F anion 722, and also greater than for a methyl group 712 (as shown in FIG. 7A). At the lower end 723 of the molecule, electrostatic potential mapping indicates a lack of electronegativity instead, as both (+) charge density and (−) charge density are indicated by shading.

FIG. 7C illustrates a $DCl^{2+}$ cation, as can be enclosed in an A site of a perovskite crystal according to an embodiment of the present invention. DFT indicates the dipole moment of $DCl^{2+}$ is approximately ~8.17 D, and its direction as indicated by arrow 727 is approximately 15° with respect to the trifold axis of the N—N'-diazabicyclo[2.2.2]octonium core. Electrostatic potential mapping of the molecule on the right side of FIG. 7C shows (−) charge distribution to be greater near the upper end 730 of the molecule, near the Cl anion 732, and also greater than for a methyl group 712 (FIG. 7A), and for an F anion 722. At the lower end 733 of the molecule, electrostatic potential mapping indicates a lack of electronegativity instead, as both (+) charge density and (−) charge density are indicated by shading.

Figure 7D:
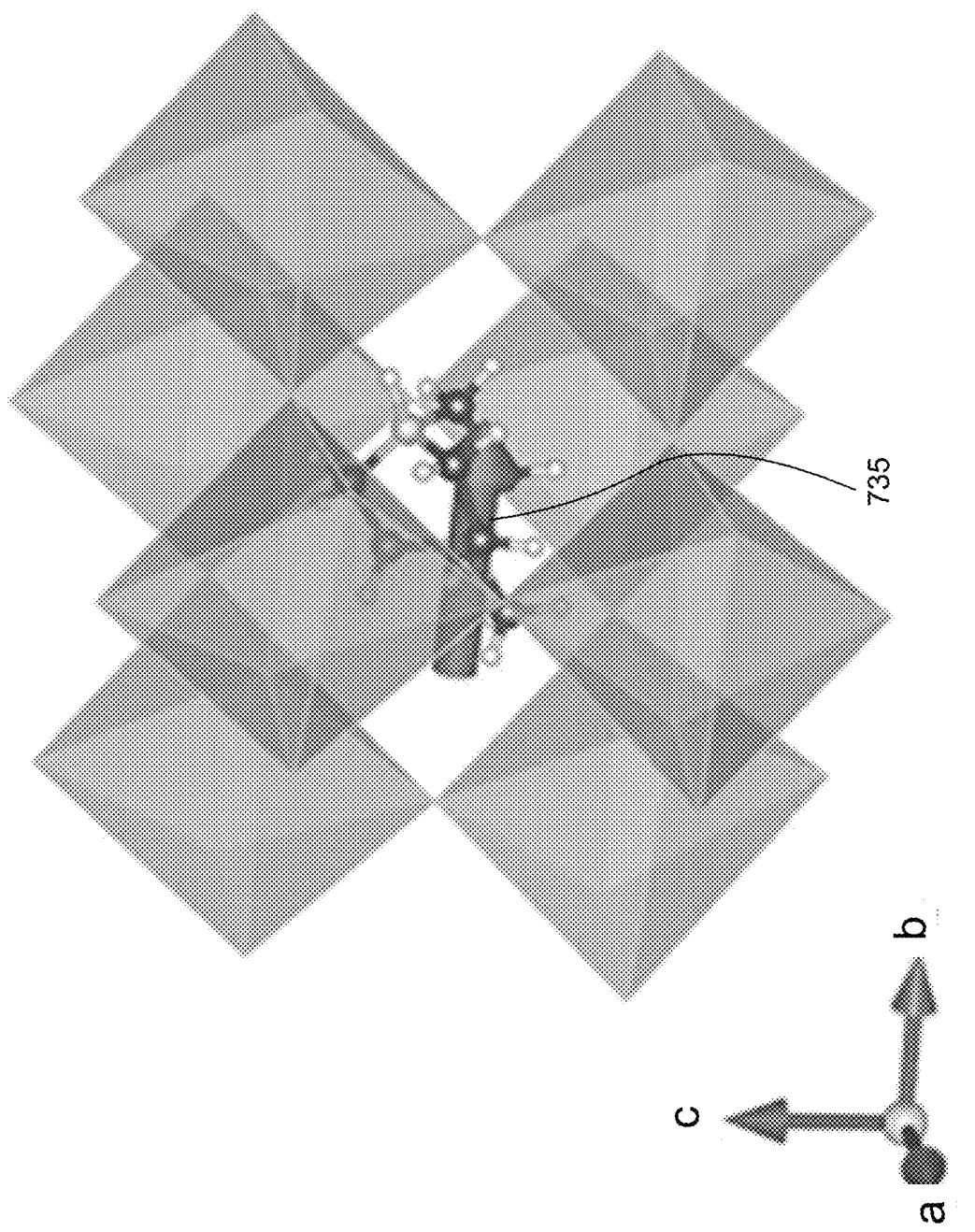
FIG. 7D-F illustrate vector of $P_s$ in three $(DR)(NH_4)(BF_4)_3$ crystals ((d), R=H; (e), R=F; (f), R=Cl).
Figure 7E:
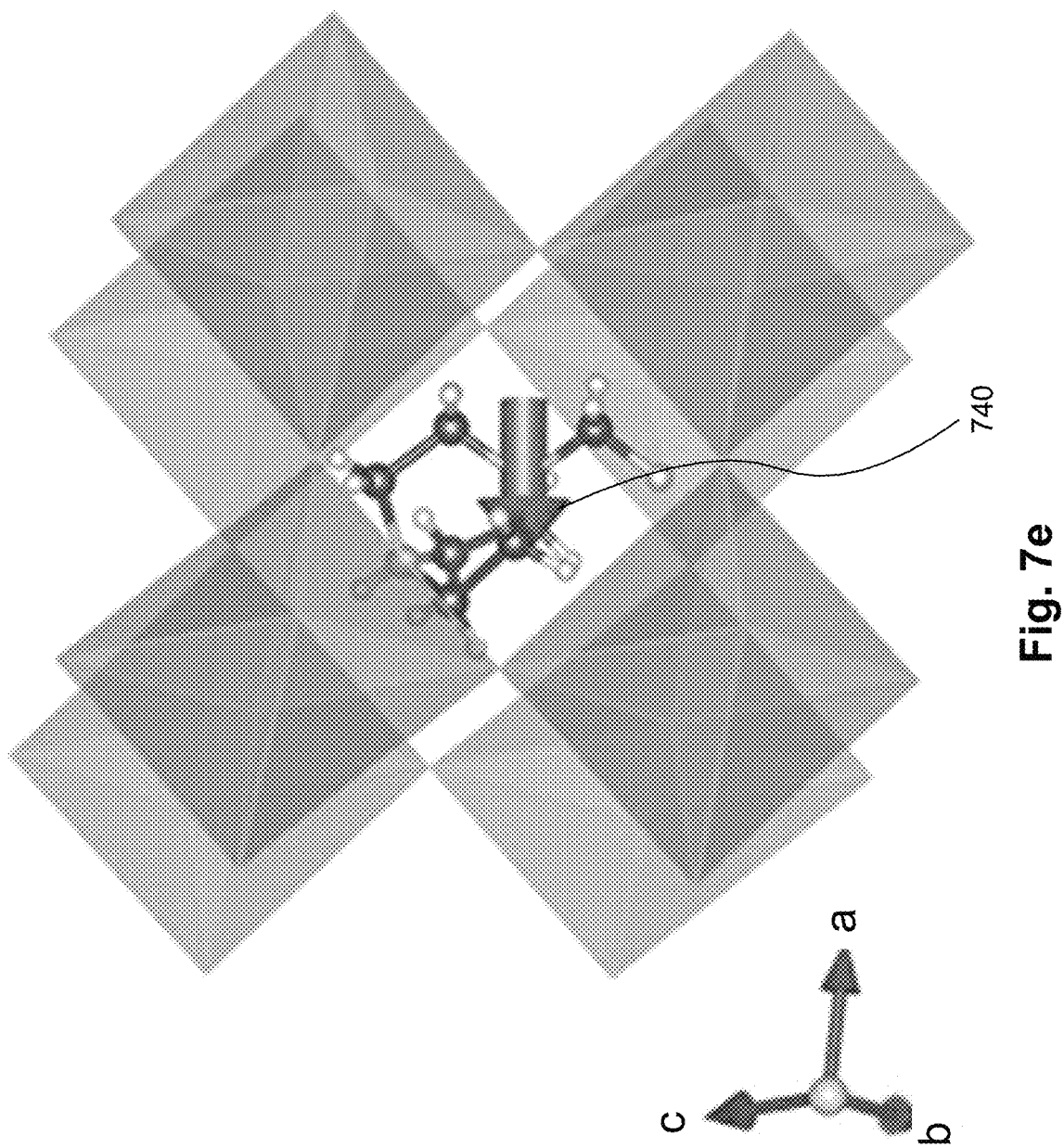
Figure 7F:
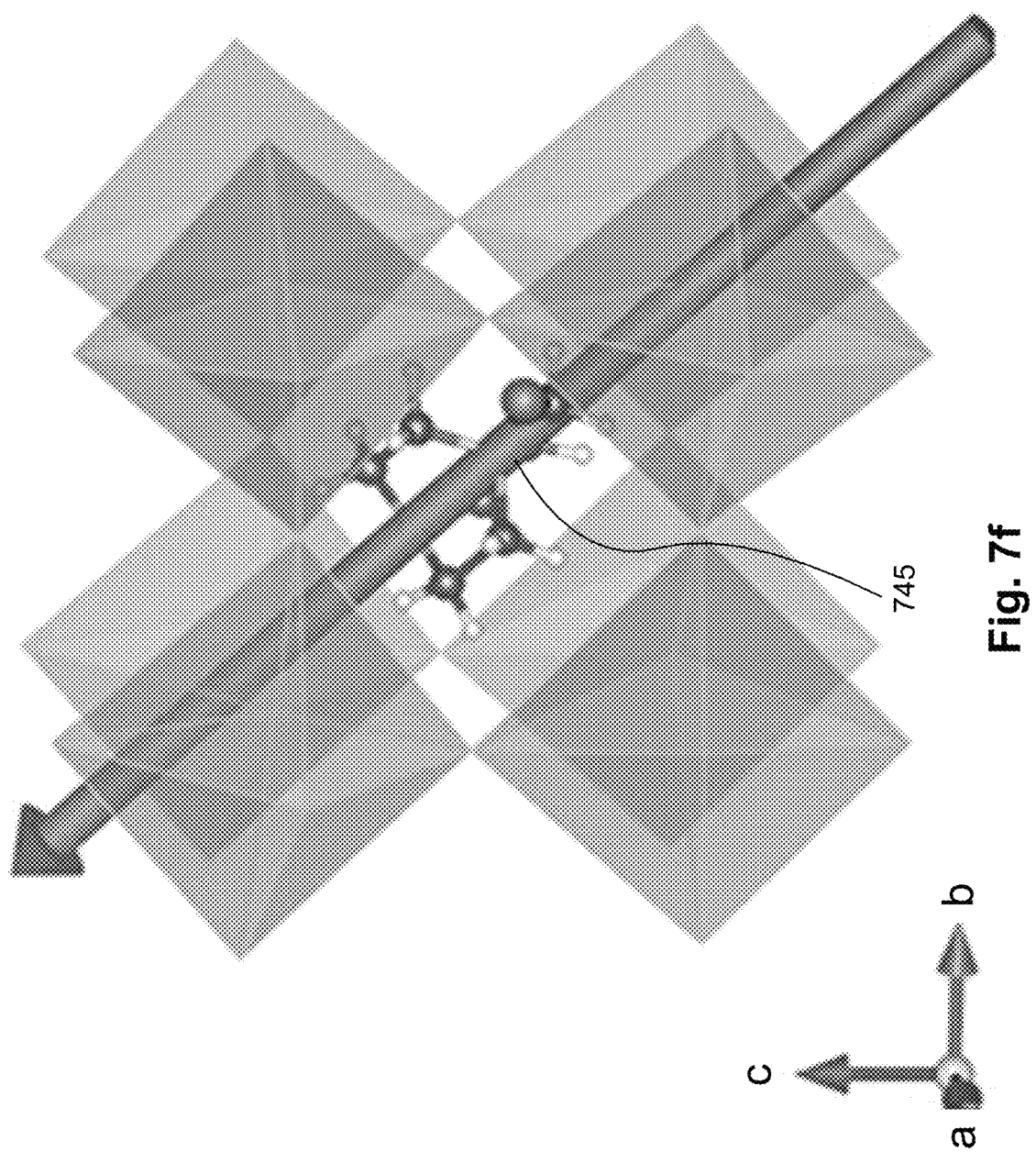
Figure 8B:
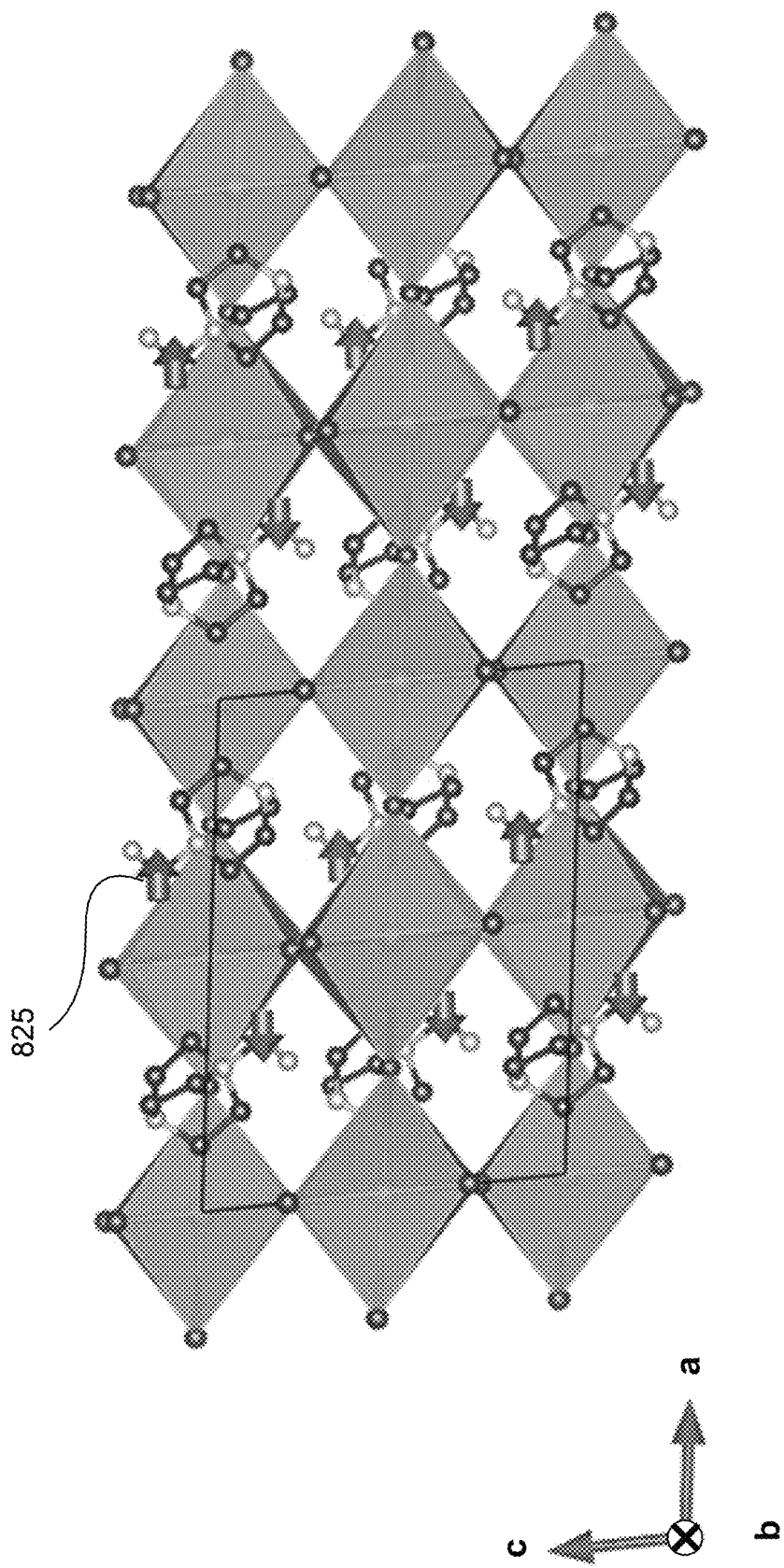
FIG. 8b illustrates the $(NH_4)(BF_4)_6$ octahedra in structure $(DF)(NH_4)(BF_4)_3$, in accordance with one embodiment of the invention.

As shown in FIG. 7F, $(DCl)(NH_4)(BF_4)_3$ exhibits the largest $P_s$ due to an optimal alignment of the large molecular dipole of $DCl^{2+}$ in the 3D noncentrosymmetric structure. The $DCl^{2+}$ molecule is aligned in the same orientation along the b axis of the 3D structure, giving rise to an overall polarization (FIG. 8A). The crystal of $(DF)(NH_4)(BF_4)_3$, exhibits the smallest P among the three cations (FIG. 7E), because the $DF^{2+}$ cations are packed in an antiparallel arrangement, resulting in a centrosymmetric crystal structure and a cancellation of $P_s$ (FIG. 8B).

FIG. 7D illustrates the polarization vector of a (DH)(NH$_4$)(BF$_4$)$_3$ cation at a site A of a perovskite crystal. The polarization vector 735 is oriented approximately parallel to lattice planes.

FIG. 7E illustrates the polarization vector of a (DF)(NH$_4$)(BF$_4$)$_3$ cation at a site A of a perovskite crystal. The polarization vector 740 is oriented approximately parallel to lattice planes and is shorter, i.e., weaker than in the cases of R=H and R=Cl.

FIG. 7F illustrates the polarization vector of a (DCl)(NH$_4$)(BF$_4$)$_3$ cation at a site A of a perovskite crystal. The polarization vector 745 is oriented approximately along the b axis of the perovskite structure, and it is larger, i.e., stronger than in the cases of R=H and R=F.

The different packing behavior than the Cl derivative can be ascribed to the smaller size of F and its less distorted perovskite framework, allowing the molecules more freedom to rotate and align in an antiparallel fashion. By comparing the molecular dipole moments with the crystal P$_s$ (FIG. 7G), it was found that only the combination of large molecular dipoles that were aligned in noncentrosymmetric crystal structures resulted in an improved P$_s$. The Cl-substituted A-site cation material could form a low-dimensional structure when I$^-$ was used as the X-site ((DCl)$_2$(NH$_4$)$_3$I$_7$). However, the polarization was found to be very small (FIGS. 8A-D), due to the undesirable molecular orientation that results in a cancellation of the dipoles. The direction and the coordinates of P$_s$ in the unit cells of the crystals are summarized in FIGS. 8A-D and Table 4.

Figure 7G:
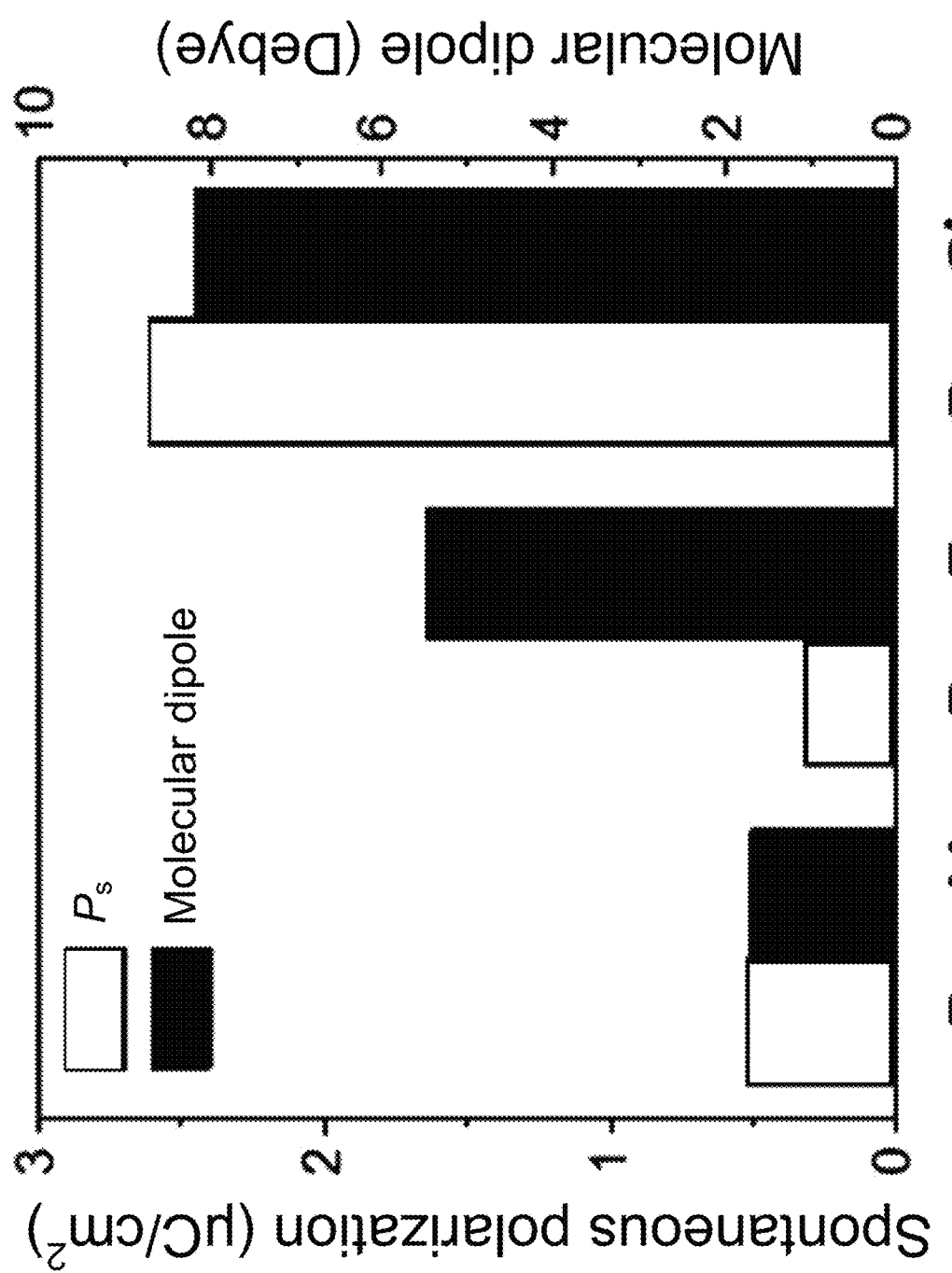
FIG. 7G is a graph depicting a comparison of the molecular dipole moments and $P_s$ of three $(DR)(NH_4)(BF_4)_3$ crystals ((d), R=H; (e), R=F; (f), R=Cl), in accordance with embodiments of the present invention.

FIG. 7G is a bar graph showing the spontaneous polarization and molecular dipole moment of organic perovskite crystals. The crystal where R=Cl shows a spontaneous polarization of approximately 8.7 μC/cm$^2$ and a molecular dipole moment of approximately 8.1 D, both greater values than if R=H and if R=F.

FIG. 8A illustrates the spontaneous polarization calculated by DFT for organic perovskite (DH)(NH$_4$)(BF$_4$)$_3$. The polar vectors 805 is set at the methyl group of DR$^{2+}$.

FIG. 8B illustrates the spontaneous polarization calculated by DFT for organic perovskite (DF)(NH$_4$)(BF$_4$)$_3$. The polar vectors 825 is set at the methyl group of DR$^{2+}$.

Figure 8C:
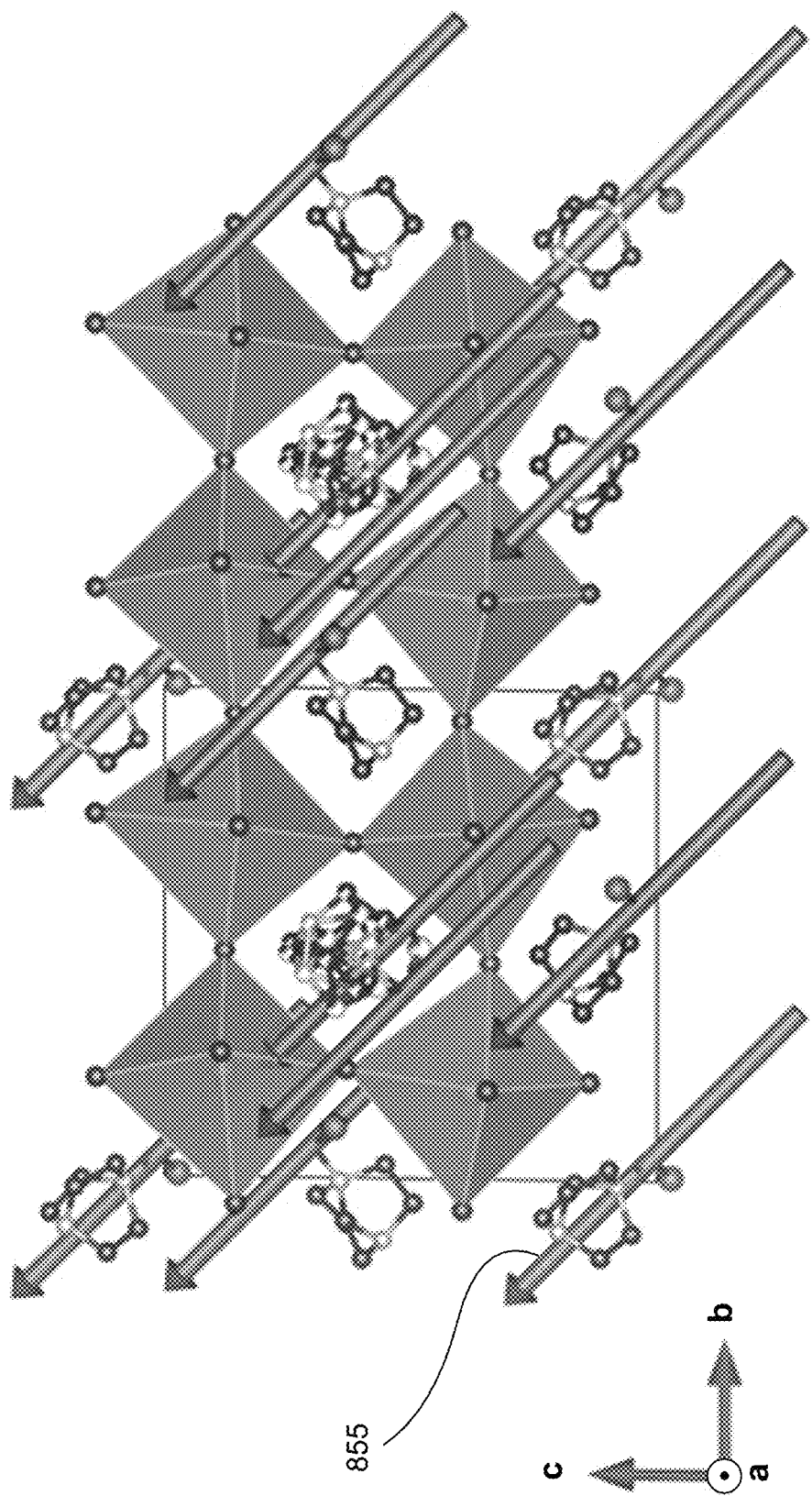
FIG. 8c illustrates the $(NH_4)(BF_4)_6$ octahedra in structure $(DCl)(NH_4)(BF_4)_3$, in accordance with one embodiment of the invention.

FIG. 8C illustrates the spontaneous polarization calculated by DFT for organic perovskite (DCl)(NH$_4$)(BF$_4$)$_3$. The polar vectors 855 set at the methyl group of DR$^{2+}$.

Figure 8D:
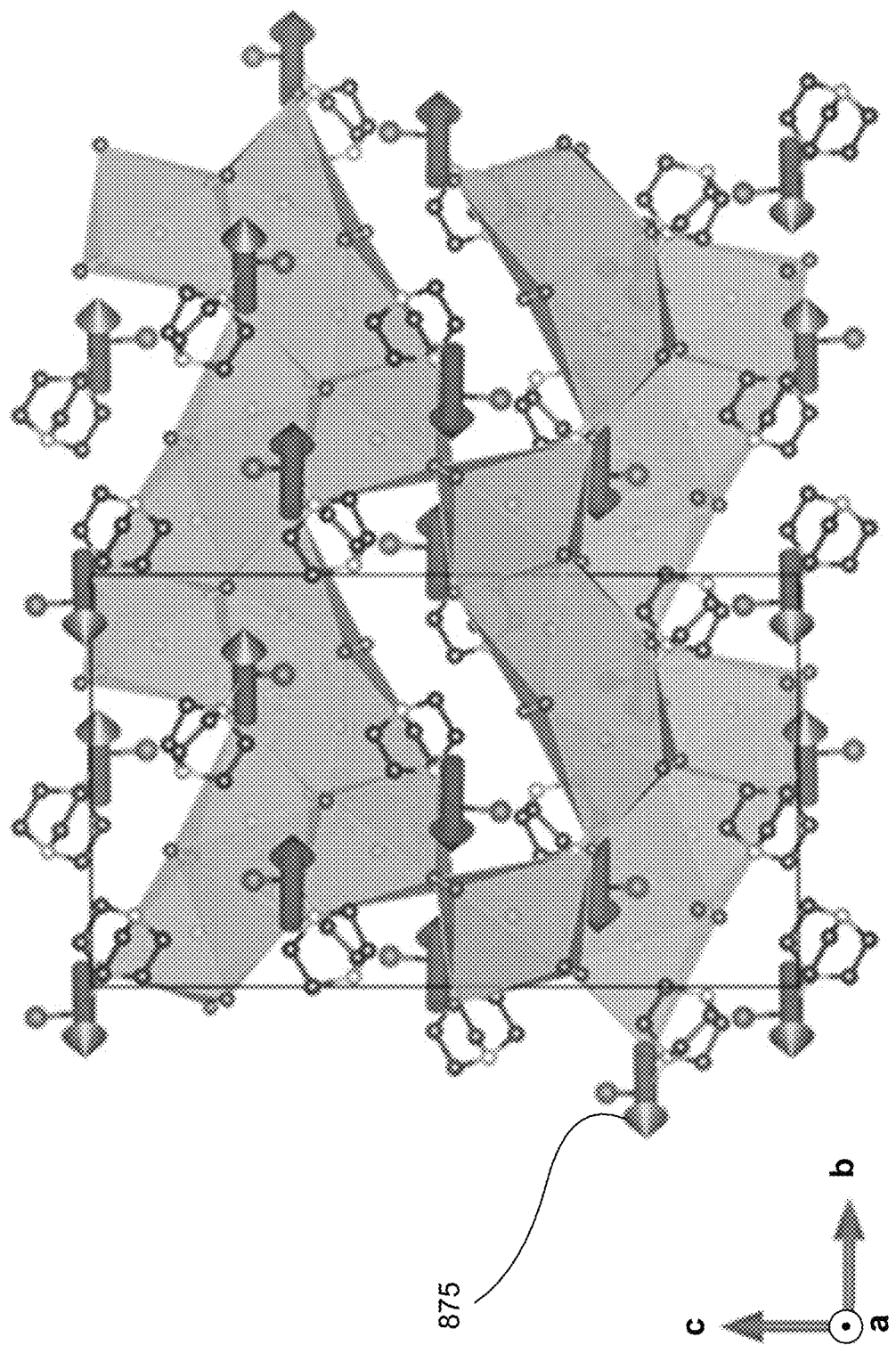
FIG. 8d illustrates the structure of $(DCl)_2(NH_4)_3I_7$.

FIG. 8D illustrates the spontaneous polarization calculated by DFT for organic perovskite (DCl)$_2$(NH$_4$)$_3$I$_7$. The polar vectors 875 are set at the methyl group of DR$^{2+}$, the polar value of (DCl)$_2$(NH$_4$)$_3$I$_7$ is multiplied by 50.

Table 4 summarizes the results of DFT calculations for the spontaneous polarizations P$_s$ of crystals. The polar coordinates and polarization values for each crystal are listed.

TABLE 4

| | x | y | z | P$_s$ (Debye) | P$_s$ (μC cm$^{-2}$)$^a$ |
|---|---|---|---|---|---|
| (DH)(NH$_4$)(BF$_4$)$_3$ | −0.0324 | 2.4187 | −0.0965 | 2.4209 | 0.52 |
| (DF)(NH$_4$)(BF$_4$)$_3$ | −1.5006 | 0.1396 | −0.0975 | 1.5102 | 0.32 |
| (DCl)(NH$_4$)(BF$_4$)$_3$ | −2.3624 | −8.9472 | 9.0157 | 12.920 | 2.61 |
| (DCl)$_2$(NH$_4$)$_3$I$_7$ | −0.0269 | −0.0359 | 0.0006 | 0.0448 | 0.0043 |

$^a$P$_s$(μC cm$^{-2}$) = P$_s$(Debye) × 3.3 × 10$^{-30}$ C · m/V$_{cell}$

Figure 9A:
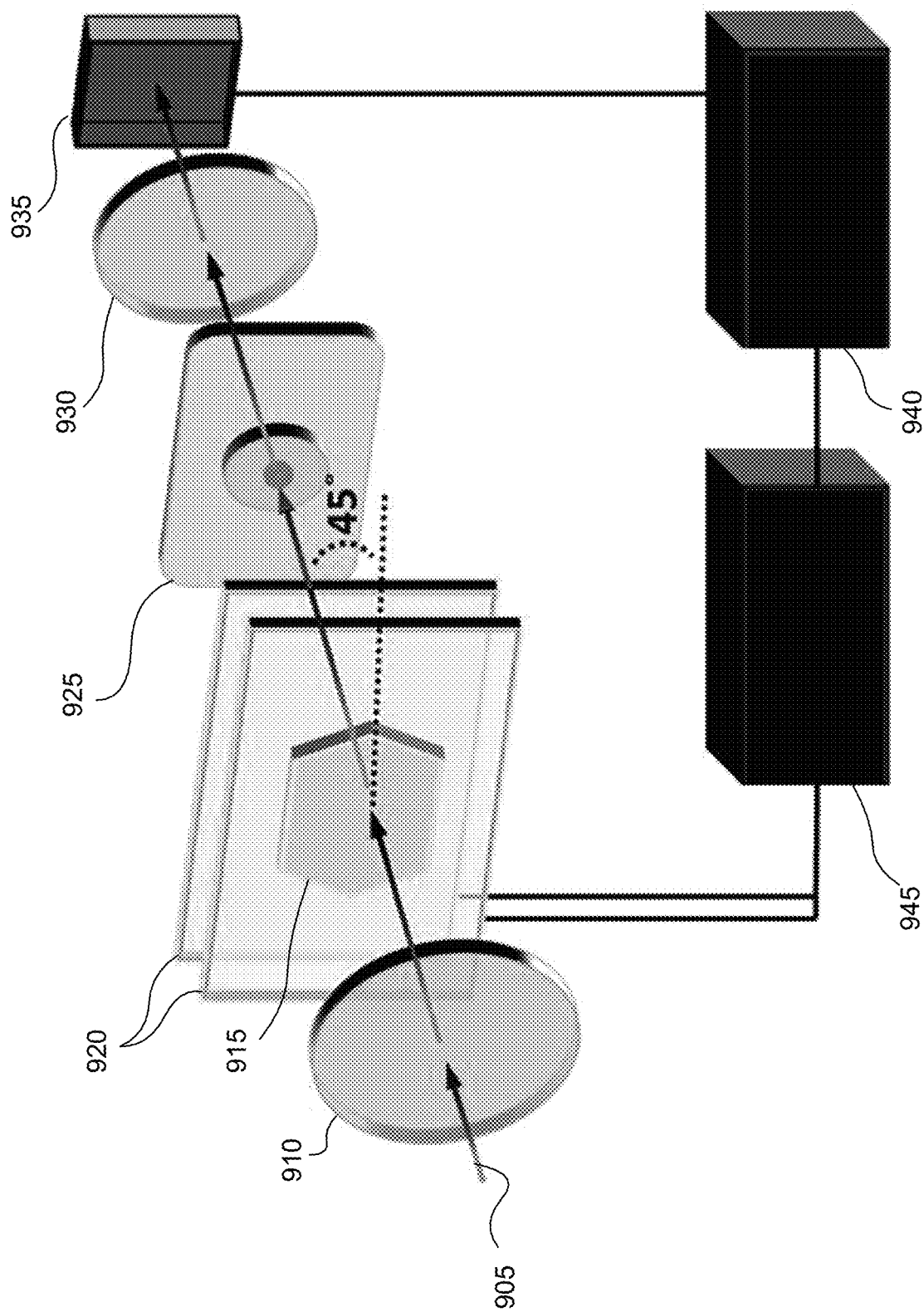
FIG. 9A is a schematic depiction of an experimental setup for determining the EO coefficient of a perovskite structural crystal.

The linear EO effect is characterized by measuring the polarization change of a laser beam transmitted through the crystal as a function of applied electric field. The EO effect is given by the linear change of the refractive index with an applied electric field, E, expressed:

$$\Delta n = \tfrac{1}{2} r_e n^3 E$$

where r$_e$ is the effective EO coefficient when an electric field is applied. The EO coefficient of (DCl)(NH$_4$)(BF$_4$)$_3$ was determined quantitatively at the standard telecom wavelength of 1550 nm using the modified Teng-Man technique (Ref. 14). A schematic of the experimental setup used is shown in FIG. 9A. Briefly, a laser beam at 1550 nm was passed through a linear polarizer to the crystal surface at an angle 45°, so that the parallel and perpendicular components of the optical field are equal in amplitude. The crystal was sandwiched between a pair of ITO electrodes to which an electric field was applied to induce the refractive index change for the light passing through the crystal. The transmitted beam was sent through a Soleil-Babinet compensator and an analyzer and finally into a Ge near-infrared photodetector connected to a lock-in amplifier. The applied electrical field was modulated by a peak-to-peak voltage (V$_{pp}$) of 10 V (electric field strength, E=5×10$^3$ Vm$^{-1}$) at a frequency of 1 kHz.

FIG. 9A illustrates an experimental setup for determining the EO coefficient of a perovskite structured crystal. A 1550 nm laser beam 905 is transmitted through a polarizer 910 at an angle 45°, so that the parallel and perpendicular components of the optical field are equal in amplitude. The beam is transmitted through a crystal sample 915, sandwiched by a pair of ITO electrodes 920, and then to a Soleil-Babinet compensator 925, an analyzer 930, and received by a Ge near-infrared photodetector 935 connected to a lock-in amplifier 940. A function generator coordinates the beam detection reception at the photodetector 935 with an electric field applied to the electrodes 920.

The power of the transmitted light increased linearly as a function of the applied AC voltage (FIG. 9B, bottom), which confirms the linear EO effect rules out the quadratic Kerr effect. The linear EO coefficient of r$_{eff}$ was calculated with the following equation (Ref 14):

$$r_{eff} = \frac{\lambda I_{ac}}{\pi V_{ac} I_c n^2} \frac{(n^2 - \sin^2 \theta)^{\frac{3}{2}}}{(n^2 - 2\sin^2 \theta)} \frac{1}{\sin^2 \theta}$$

where θ=45°, V$_{ac}$=V$_{pp}$ sin θ, I$_{ac}$ is the amplitude of the modulated light intensity and is the half intensity of the maximum intensity of the output laser at the detector.

Using this method, the EO coefficient of (DCl)(NH$_4$)(BF$_4$)$_3$ was found to be 20 pm V$^{-1}$ at 1 kHz and was independent of the operating voltage (FIG. 9B, top), which means that this EO process is second-order nonlinearly. This EO coefficient is higher than that of layered hybrid perovskites (Ref 2c). and is comparable to conventional nonlinear crystals (Refs. 1a, 15). In contrast, the linear EO effect of (DH)(NH$_4$)(BF$_4$)$_3$ and (DCl)$_2$(NH$_4$)$_3$I$_7$ crystals were too weak to detect due to the small P$_s$.

Figure 9B:
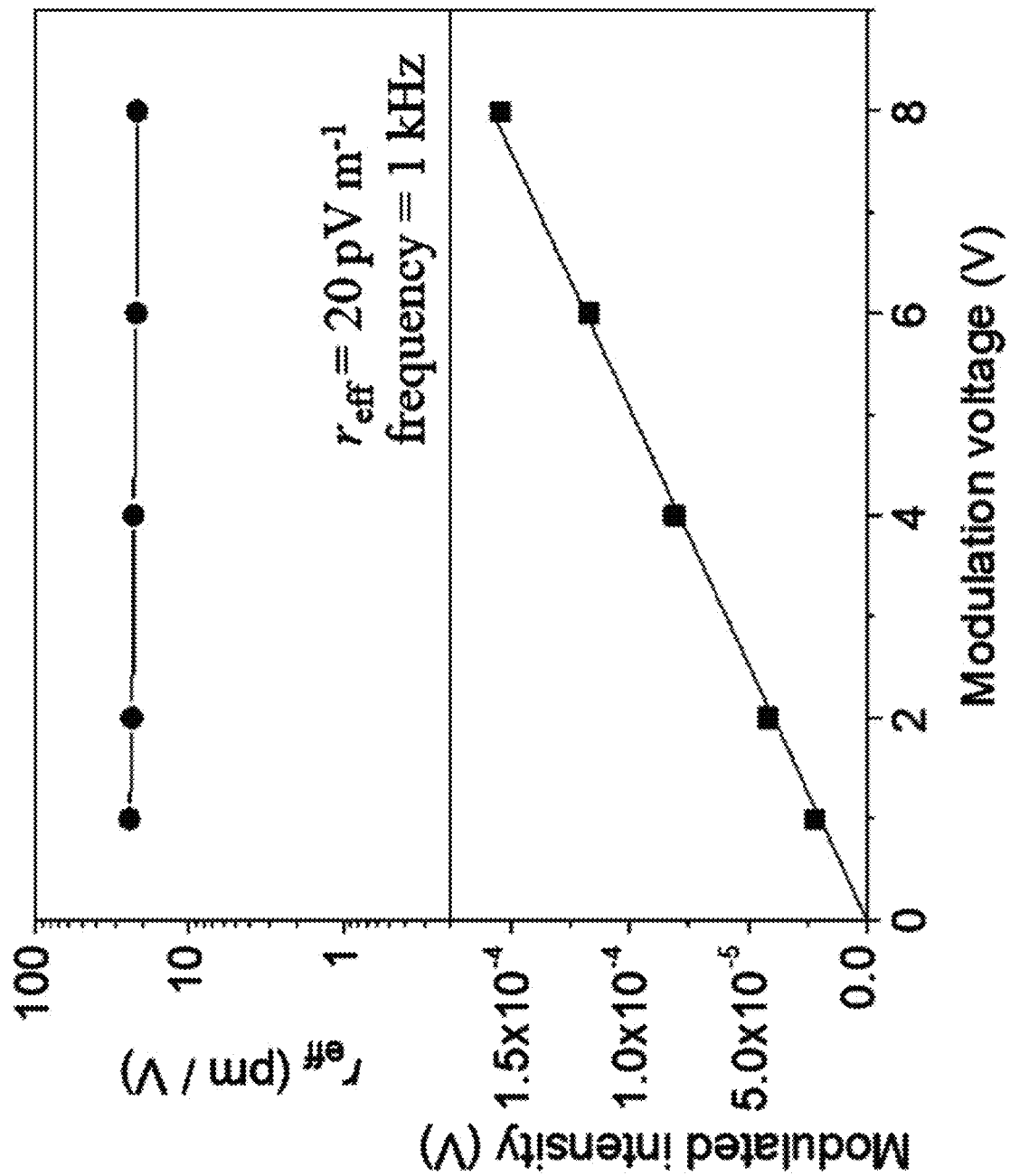
FIG. 9B depicts a plot of EO coefficient at different modulated voltage (top graph) and a plot the linear growth of the transmitted light power increasing with the modulation voltage (bottom graph).

FIG. 9B is a graph showing the effect of applying a voltage to the crystal, in terms of transmission intensity and linearity. As a modulation voltage is applied to a (DCl)(NH$_4$)(BF$_4$)$_3$ crystal, the intensity of a transmitted 1550 nm beam increases linearly, as measured by a photodiode. A linearity can also be seen on an EO coefficient scale, where the value of r$_{eff}$ is shown to be approximately constant at 20 pmV$^{-1}$ over a range of modulation voltages from 0 to 8V.

In summary, highly polarizable organic perovskites have been prepared by introducing halogen functional groups in the A-site cation. It has been demonstrated that the (DCl)(NH$_4$)(BF$_4$)$_3$ crystal exhibits a strong linear EO effect with an effective EO coefficient of 20 pmV$^{-1}$, which is 10 times higher than that of metal halide perovskites and is 1.5 fold enhancement compared to previously reported organic perovskites, (DH)(NH$_4$)I$_3$. By combining experimentally determined crystallographic information with DFT simulations, it was shown that the large EO response originates from the ability of the crystal to align large molecular dipoles within the 3D perovskite structure. Although the EO response of the organic perovskite (DCl)(NH$_4$)(BF$_4$)$_3$ approaches that of LiNbO$_3$ ($r_{eff}$≈30 pm V$^{-1}$), the 3D organic perovskites of the present invention are more convenient to handle than LiNbO$_3$, as they are solution processed and compatible with silicon. These findings highlight the potential of rationally-designed all-organic perovskites for use in on-chip modulators.

Although the present invention has been described with reference to specific features and embodiments thereof, it is evident that various modifications and combinations can be made thereto without departing from the invention. The specification and drawings are, accordingly, to be regarded simply as an illustration of the invention as defined by the appended claims, and are contemplated to cover any and all modifications, variations, combinations or equivalents that fall within the scope of the present invention.

REFERENCES

[1] a) E. L. Wooten, K. M. Kissa, A. Yi-Yan, E. J. Murphy, D. A. Lafaw, P. F. Hallemeier, D. Maack, D. V. Attanasio, D. J. Fritz, G. J. McBrien, D. E. Bossi, *IEEE J. Sel. Top. Quantum Electron.* 2000, 6, 69; b) I. S. Amiri, S. R. B. Azzuhri, M. A. Jalil, H. M. Hairi, J. Ali, M. Bunruangses, P. Yupapin, *Micromachines* 2018, 9, 452.

[2] a) C. Wang, M. Zhang, X. Chen, M. Bertrand, A. S. Ansari, S. Chandrasekhar, P. Winzer, M. M. Lončar, *Nature* 2018, 562, 101; b) A. D. Dupuy, Y. Kodera, J. E. Garay, *Adv. Mater.* 2016, 28, 7970; c) Y. Gao, G. Walters, Y. Qin, B. Chen, Y. Min, A. Seifitokaldani, B. Sun, P. Todorovic, M. I. Saidaminov, A. Lough, S. Tongay, S. Hoogland, E. H. Sargent, *Adv. Mater.* 2019, 31, 1808336.

[3] a) R. S. Weis, T. K. Gaylord, *Appl. Phys. A* 1985, 37, 191; b) S. Abel, F. Eltes, J. E. Ortmann, A. Messner, P. Castera, T. Wagner, D. Urbonas, A. Rosa, A. M. Gutierrez, D. Tulli, P. Ma, B. Baeuerle, A. Josten, W. Heni, D. Caimi, L. Czornomaz, A. A. Demkov, J. Leuthold, P. Sanchis, J. Fompeyrine, *Nat. Mater.* 2019, 18, 42.

[4] a) S. Abel, T. Stoferle, C. Marchiori, C. Rossel, M. D. Rossell, R. Erni, D. Caimi, M. Sousa, A. Chelnokov, B. J. Offrein, J. Fompeyrine, *Nat. Commun.* 2013, 4, 1671; b) L. Chen, R. M. Reano, *Opt. Express* 2012, 20, 4032.

[5] a) S. R. Marder, L.-T. Cheng, B. G. Tiemann, A. C. Friedli, M. Blanchard-Desce, J. W. Perry, J. Skindhøj, *Science* 1994, 263, 511; b) L. R. Dalton, *J. Phys.: Condens. Matter* 2003, 15, R897; c) S. R. Marder, B. Kippelen, A. K.-Y. Jen, N. Peyghambarian, *Nature* 1997, 388, 845.

[6] L. R. Dalton, A. W. Harper, B. H. Robinson, *Proc. Natl. Acad. Sci. USA* 1997, 94, 4842.

[7] C. A. Bremner, M. Simpson, W. T. A. Harrison, *J. Am. Chem. Soc.* 2002, 124, 10960.

[8] H.-Y. Ye, Y.-Y. Tang, P.-F. Li, W.-Q. Liao, J.-X. Gao, X.-N. Hua, H. Cai, P.-P. Shi, Y.-M. You, R.-G. Xiong, *Science* 2018, 361, 151.

[9] Y. Gao, S. M. Alsadat, A. Johnston, C. Zheng, G. Walters, Q. Feng, X. Wang, M.-J. Sun, A. M. Najarian, D. Xue, Y.-K. Wang, M. I. Saidaminov, O. Voznyy, S. Hoogland, E. H. Sargent, Electro-optic Modulation using Metal-free Perovskites, paper in submission.

[10] a) H. Wang, H. Liu, Z. Zhang, Z. Liu, Z. Lv, T. Li, W. Ju, H. Li, X. Cai, H. Han, npj *Comput. Mater.* 2019, 5, 17; b) F. Wang, *Phys. Rev. B* 1999, 59, 9733.

[11] a) H.-Y. Zhang, Y.-Y. Tang, P.-P. Shi, R.-G. Xiong, *Acc. Chem. Res.* 2019, 52, 1928; b) Y. Ai, X.-G. Chen, P.-P. Shi, Y.-Y. Tang, P.-F. Li, W.-Q. Liao, R.-G. Xiong, *J. Am. Chem. Soc.* 2019, 141, 4474.

[12] V. M. Goldschmidt, *Naturwissenschaften* 1926, 14, 477.

[13] a) M. W. Lufaso, P. M. Woodward, *Acta Crystallogr., Sect. B: Struct. Sci.* 2004, 60, 10; b) Alonso, J.; b) M. Martinez-Lope, M. Casais, M. Fernandez-Diaz, *Inorg. Chem.* 2000, 39, 917.

[14] a) C. C. Teng, H. T. Man, *Appl. Phys. Lett.* 1990, 56, 1734; b) Y. Shuto, M. Amano, *J. Appl. Phys.* 1995, 77, 4632.

[15] a) J. L. Casson, K. T. Gahagan, D. A. Scrymgeour, R. K. Jain, J. M. Robinson, V. Gopalan, R. K. Sander, *J. Opt. Soc. Am. B* 2004, 21, 1948; b) A. Yariv, P. Yeh, *Photonics: Optical Electronics in Modern Communications*, Oxford University Press, UK 2007.

[16] G. Veronique, S. Graham, (Oxford University Innovation) U.K. WO2014/68341, 2014.

[17] W. Kohn, L. J. Sham, *Phys. Rev.* 1965, 140, A1133.

[18] J. P. Perdew, K. Burke, M. Ernzerhof, *Phys. Rev. Lett.* 1996, 77, 3865.

[19] S. Goedecker, M. Teter, J. Hutter, *Phys. Rev. B* 1996, 54, 1703.

[20] S. Grimme, J. Antony, S. Ehrlich, H. Krieg, *J. Chem. Phys.* 2010, 132, 154104

[21] a) B. G. Lippert, J. H. Parrinello, Michele, *Mol. Phys.* 1997, 92, 477; b) J. VandeVondele, M. Krack, F. Mohamed, M. Parrinello, T. Chassaing, J. Hutter, *Comput. Phys. Commun.* 2005, 167, 103; c) J. Hutter, M. Iannuzzi, F. Schiffmann, J. VandeVondele, *WIREs Comput. Mol. Sci.* 2014, 4, 15.

[22] S. Luber, *J. Chem. Phys.* 2014, 141, 234110.

What is claimed is:

1. A 3D organic perovskite having the Formula (I):

$$ABX_3 \qquad (I)$$

wherein:
A has the formula DR$^{2+}$, wherein DR$^{2+}$ is:

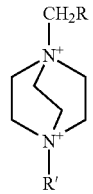

wherein
R is F, Cl, Br, CN, or OH; and
R' is H or CH$_3$;
B is NH$_4^+$; and
X is BF$_4^-$ or PF$_6^-$.

2. The organic perovskite of claim 1, wherein R is F or Cl.

3. The organic perovskite of claim 1 or 2, wherein X is BF$_4^-$.

4. The organic perovskite of claim 1, which is (DCl)(NH$_4$)(BF$_4$)$_3$.

5. The organic perovskite of claim 1, which is (DF)(NH$_4$)(BF$_4$)$_3$.

* * * * *